(12) United States Patent
Paternostre et al.

(10) Patent No.: US 9,382,306 B2
(45) Date of Patent: Jul. 5, 2016

(54) OCTAPEPTIDE COMPOUNDS DERIVED FROM SOMATOSTATIN AND THE THERAPEUTIC USE THEREOF

(75) Inventors: Marie-Thérèse Paternostre, Verrières le Buisson (FR); Jean-Christophe Cintrat, Igny (FR); Céline Valery, Barelone (ES); Stéphane Roux, Nice (FR); Bernard Rousseau, Levallois Perret (FR); Maarten Ijsselstijn, Groningen (NL); Roland Cherif-Cheikh, Castelldefels (ES); Franck Artzner, Cesson Sevigne (FR)

(73) Assignees: IPSEN PHARMA S.A.S., Boulogne-Billancourt (FR); COMMISSARIAT A L'ENERGIE ATOMIQUE (CEA), Paris (FR); LE CENTRE NATIONAL DE RECHERCHE SCIENTIFIQUE (CNRS), Paris (FR)

( * ) Notice: Subject to any disclaimer, the term of this patent is extended or adjusted under 35 U.S.C. 154(b) by 1107 days.

(21) Appl. No.: 13/121,928

(22) PCT Filed: Sep. 29, 2009

(86) PCT No.: PCT/FR2009/001162
§ 371 (c)(1),
(2), (4) Date: Mar. 30, 2011

(87) PCT Pub. No.: WO2010/037930
PCT Pub. Date: Apr. 8, 2010

(65) Prior Publication Data
US 2011/0178013 A1    Jul. 21, 2011

(30) Foreign Application Priority Data

Sep. 30, 2008   (EP) .................................... 08290917

(51) Int. Cl.
| | |
|---|---|
| A61K 38/31 | (2006.01) |
| A61P 5/02 | (2006.01) |
| C07K 14/655 | (2006.01) |
| A61K 38/12 | (2006.01) |
| C07K 5/00 | (2006.01) |
| C07K 7/00 | (2006.01) |
| C07K 16/00 | (2006.01) |
| C07K 17/00 | (2006.01) |
| C07K 14/665 | (2006.01) |
| A61K 38/00 | (2006.01) |

(52) U.S. Cl.
CPC ............... *C07K 14/665* (2013.01); *A61K 38/00* (2013.01)

(58) Field of Classification Search
CPC ........... C07K 7/00; A61K 38/04; A61K 38/08
See application file for complete search history.

(56) References Cited

U.S. PATENT DOCUMENTS

2009/0004195 A1 *  1/2009  Vranic et al. .............. 424/139.1

FOREIGN PATENT DOCUMENTS

| CN | 200810124167 | 11/2008 |
|---|---|---|
| RU | 2160741 | 12/2000 |
| RU | 2242481 | 12/2004 |
| RU | 2328504 | 7/2008 |
| RU | 2547940 | 4/2015 |
| WO | WO 97/01579 | 1/1997 |
| WO | WO 99/65942 | 12/1999 |
| WO | WO 02/072602 | 9/2002 |

OTHER PUBLICATIONS

FDA "FDA Approves New Drug to Treat Rare Disease, Acromegaly". FDA News Release. Published Aug. 31, 2007.*
Pandit et al. "Self-assembly of the octapeptide lanreotide and lanreotide-based derivatives: the role of the aromatic residues" J. Peptide Sci. 14:66-75. Published Oct. 11, 2007.*
Anonymous. "Lanreotide". From <en.wikipedia.org/wiki/Lanreotide>. First published Mar. 3, 2007.*
Murphy et al. "Inhibition of rat prostate tumor growth by an octapeptide analog of somatostatin" Life Sciences 40:2515-2522. Published 1973.*
Walker, et al. *Peptides* 8: 869-875 (1987).

* cited by examiner

*Primary Examiner* — Christina Bradley
*Assistant Examiner* — Zachary J Miknis
(74) *Attorney, Agent, or Firm* — Hunton & Williams LLP

(57) ABSTRACT

The present invention relates to novel octapeptide compounds of general formula (I): H-2-Nal$^1$-cyclo(Cys$^2$-Tyr$^3$-AA$^4$-Lys$^5$-Val$^6$-Cys$^7$)-Thr$^8$-NH$_2$. Since these products have a good affinity for certain somatostatin receptor subtypes, they are particularly advantageous for treating pathological states or diseases in which one (or more) somatostatin receptor(s) is (are) involved. These compounds furthermore have physiochemical properties that make it possible to envisage them in diverse solutions for the formulation of medicaments, for example as a pharmaceutically acceptable carrier. The invention also relates to pharmaceutical compositions containing said products and to the use thereof for the preparation of a medicament.

7 Claims, No Drawings

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial sequence
<220> FEATURE:
<223> OTHER INFORMATION: Somatostatin-derived octapeptide
<220> FEATURE:
<221> NAME/KEY: MISC
<222> LOCATION: (1)..(1)
<223> OTHER INFORMATION: Xaa is 2-naphthylalanine
<220> FEATURE:
<221> NAME/KEY: MISC
<222> LOCATION: (2)..(7)
<223> OTHER INFORMATION: Residues 2-7 are cyclical.
<220> FEATURE:
<221> NAME/KEY: MISC
<222> LOCATION: (4)..(4)
<223> OTHER INFORMATION: Xaa is any amino acid.

<400> SEQUENCE: 1

Xaa Cys Tyr Xaa Lys Val Cys Thr
1               5
```

OCTAPEPTIDE COMPOUNDS DERIVED FROM SOMATOSTATIN AND THE THERAPEUTIC USE THEREOF

This application is a national stage of filing of PCT/FR2009/001162, filed Sep. 29, 2009, the subject matter of which is incorporated herein in its entirety. This application further claims priority to EP08290917.7 filed Sep. 30, 2008, the subject matter of which is incorporated herein in its entirety.

FIELD OF INVENTION

The present invention relates to novel octapeptide compounds. As these products have a good affinity for certain sub-types of somatostatin receptors, they are particularly useful for treating the pathological states or diseases in which one (or more) of the somatostatin receptors is (are) involved. These compounds moreover have physico-chemical properties making it possible to envisage them in various solutions for the formulation of medicaments, for example as a pharmaceutically-acceptable support. The invention also relates to pharmaceutical compositions containing said products and their use for the preparation of a medicament.

BACKGROUND OF INVENTION

Somatostatin (SST) is a cyclic tetradecapeptide which was isolated for the first time from the hypothalamus as a substance which inhibits the growth hormone (Brazeau P. et al., Science 1973, 179, 77-79). It also operates as a neurotransmitter in the brain (Reisine T. et al., Neuroscience 1995, 67, 777-790; Reisine et al., Endocrinology 1995, 16, 427-442). The heterogeneity of the biological functions of somatostatin and the structure-activity relationships of its peptide analogues have led to the discovery of 5 sub-types of membrane receptors (Yamada et al., Proc. Natl. Acad. Sci. U.S.A, 89, 251-255, 1992; Raynor, K. et al, Mol. Pharmacol., 44, 385-392, 1993). Molecular cloning has made it possible to show that the bioactivity of somatostatin depends directly on these five sub-types of receptors.

The functional roles of these receptors are currently being actively studied. Preferential activation of sub-types 2 and 5 has been associated with the suppression, in the adenomas secreting these hormones, of the growth hormone GH (acromegalia), of TSH and prolactin; but the precise role of each sub-type remains to be determined

DETAILED DESCRIPTION OF THE INVENTION

Among the pathological disorders associated with somatostatin (Moreau J. P. et al., Life Sciences 1987, 40, 419; Harris A. G. et al., The European Journal of Medicine, 1993, 2, 97-105), there can be mentioned for example: acromegalia, hypophyseal adenomas, Cushing's disease, gonadotrophinomas and prolactinomas, catabolic side-effects of glucocorticoids, diabetes, diabetic retinopathy, diabetic nephropathy, hyperthyroidism, gigantism, endocrinic gastroenteropancreatic tumours including carcinoid syndrome, VIPoma, insulinoma, nesidioblastosis, hyperinsulinemia, glucagonoma, gastrinoma and Zollinger-Ellison's syndrome, GRFoma as well as acute bleeding of the oesophageal varices, gastroesophageal reflux, gastroduodenal reflux, pancreatitis, enterocutaneous and pancreatic fistulae but also diarrhoeas, refractory diarrhoeas of acquired immunodeficiency syndrome, chronic secretory diarrhoea, diarrhoea associated with irritable bowel syndrome, disorders linked with gastrin releasing peptide, secondary pathologies with intestinal grafts, portal hypertension as well as haemorrhages of the varices in patients with cirrhosis, gastro-intestinal haemorrhage, haemorrhage of the gastroduodenal ulcer, Crohn's disease, systemic scleroses, dumping syndrome, small intestine syndrome, hypotension, scleroderma and medullar thyroid carcinoma, diseases linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumours, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, as well as Alzheimer's disease. Osteoporisis can also be mentioned.

These days, increasing attention is being given to peptides having an affinity for the somatostatin receptors. Thus, lanreotide has been much studied for the treatment of diseases linked to growth hormone (Cendros J M, Peraire C, Troconiz I F, Obach R. Pharmacokinetics and population pharmacodynamic analysis of lanreotide Autogel. Metabolism. 2005 October, 54(10), 1276-81).

The need to find alternatives to existing solutions therefore constitutes a major challenge. The present invention comes within this context.

The applicant therefore proposes novel octapeptide compounds having a good affinity for the somatostatin receptors and/or physico-chemical properties making it possible to envisage various solutions for the formulation of medicaments.

The compounds according to the invention have numerous advantages, in particular at least one of the following characteristics:
their affinity for the somatostatin receptors,
their rheology allowing associated ranges of viscosites linked to the comfort of injection,
their ability to be used as a formulation support,
their capability of self-assembly in the form of nanotubes of variable and monodisperse diameters,
their capability of self-assembly in the form of fibres,
their various degrees of solubility in water.

Therefore a subject of the present invention is an octapeptide compound of general formula (I)

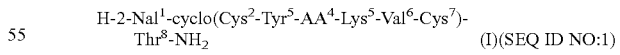
(I)(SEQ ID NO:1)

in which $AA^4$ represents an amino acid radical bound to the amino acids $Tyr^3$ and $Lys^5$ according to the formula

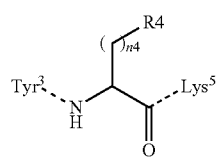

in which n4 represents an integer from 0 to 3 and R4 represents a hydrogen atom, an alkyl, cycloalkyl, aryl or heteroaryl radical, the aryl and heteroaryl radicals being optionally substituted by one or more identical or different radicals chosen from arylazo, halo, nitro, hydroxy, aryl, OR41;

R41 represents a

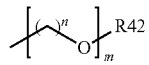

radical in which R42 represents an alkyl radical or a hydrogen atom, n is an integer from 2 to 4, and m is an integer from 1 to 4;

it being understood that all the amino acids can be of D or L configuration, with the exception of the compounds H-D-2-Nal$^1$-cyclo(Cys$^2$-Tyr$^3$-β-(3-pyridyl)-D-Ala$^4$-Lys$^5$-Val$^6$-Cys$^7$)-Thr$^8$-NH$_2$, H-D-2-Nal$^1$-cyclo(Cys$^2$-Tyr$^3$-D-Phe$^4$-Lys$^5$-Val$^6$-Cys$^7$)-Thr$^8$-NH$_2$, H-D-2-Nal$^1$-cyclo(Cys$^2$-Tyr$^3$-D-Trp$^4$-Lys$^5$-Val$^6$-Cys$^7$)-Thr$^8$-NH$_2$ and their salts, or a pharmaceutically acceptable salt of this compound.

According to the present invention, by amino acid radical is meant the radical formed by an amino acid engaged in peptide bonds by means of its amine and acid functions. Thus, an amino acid radical having R as side chain will have for radical the radical of formula —NH—CH(R)—C—(O)—.

According to the present invention, the amino acids represented by their three-letter code in a general formula, or as such, or also as radicals, can be of D or L configuration, if nothing is specified.

Moreover, according to the present invention and in accordance with convention, the designation of the peptides exemplified by their amino acid sequence represented by their three-letter code, mentions the L configuration amino acids without specifying anything whilst the D amino acids are explicitly indicated by the letter D preceding the three-letter code of the amino acid considered.

Within the meaning of the present invention, unless otherwise specified, by alkyl is meant a linear or branched alkyl radical comprising 1 to 6 carbon atoms such as methyl, ethyl, propyl, isopropyl, butyl, isobutyl, tert-butyl, pentyl, or hexyl, and preferably 1 to 4 carbon atoms.

By cycloalkyl, is meant a cyclic radical comprising 3 to 7 carbon atoms bound together by single bonds, such as cyclopropyl, cyclobutyl, cyclopentyl, cyclohexyl or cycloheptyl. This radical is optionally substituted by an alkyl radical as defined above. Preferentially the cycloalkyl radical comprises between 4 and 6 methylene members, such as cyclobutyl, cyclopentyl or cyclohexyl. Very preferentially, the cycloalkyl radical represents a cyclohexyl radical.

By aryl, is meant an unsaturated carbocyclic system comprising at least one aromatic ring, and preferably a radical chosen from phenyl, naphthyl, anthryl (or anthracenyl) and fluorenyl.

By arylazo, within the meaning of the present invention is meant a radical of formula aryl-N=N—, in which the aryl radical is as defined above. Preferably, the arylazo radical represents the phenylazo radical.

By heteroaryl with the meaning of the present invention, is meant an unsaturated aromatic ring comprising one or more identical or different heteroatoms chosen from N, O and S, such as the pyridinyl, pyrimidinyl, furyl, thienyl, benzothienyl, oxazolyl, benzoxazolyl, isoxazolyl, thiazolyl, pyrolyl, pyrazolyl, imidazolyl, triazolyl, tetrazolyl and quite particularly thienyl, benzothienyl and imidazolyl radicals.

According to the present invention, the expression pharmaceutically acceptable salt defines addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphonate, pamoate and stearate. For other examples of pharmaceutically acceptable salts, reference can be made to "Salt selection for basic drugs", Int. J. Pharm. (1986), 33, 201-217.

According to the present invention, the amino acids represent the amino acids of D or L configuration known to a person skilled in the art, represented here according to their usual nomenclature and the modified synthetic analogues on the side chains of said amino acids among which:

β-3-(3-benzothienyl)-Ala, β-(2-thienyl)-Ala, β-(1-naphthyl)-Ala, β-(2-naphthyl)-Ala or 2-Nal, β-(9-anthryl)-Ala, β-(2-fluorenyl)-Ala represents an alanine substituted in β position respectively by a benzothienyl radical in its position 3, thienyl in its position 2, naphthyl in its position 1, naphthyl in its position 2, anthryl in its position 9, and fluorenyl in its position 2;

Ph-Gly or Phg represents a glycine substituted by a phenyl radical;

Homo-Phe or Homophe represents a phenylalanine the side chain of which is lengthened by a methylene member; and, p-Br-Phe, p-F-Phe, p-Nitro-Phe, p-Ph-Phe; p-O-2-(2-methoxyethoxy)ethoxy-Phe, m-Br-Phe, m-F-Phe, o-Br-Phe, o-F-Phe, 3,5-diF-Phe represent a phenylalanine the phenyl nucleus of which is substituted respectively in para position by a bromine, fluorine atom, a nitro, phenyl and O-2-(2-methoxyethoxy)ethoxy radical, in meta position by a bromine and fluorine atom, in ortho position by a bromine and fluorine atom and in positions 3 and 5 by two fluorine atoms.

Preferentially, a more particular subject of the invention is a compound as defined above in which n4 represents an integer from 0 to 2 and R4 represents an alkyl, cycloalkyl, aryl or heteroaryl radical, the aryl and heteroaryl radicals being optionally substituted by one or more identical or different radicals chosen from arylazo, halo, nitro, hydroxy, aryl, OR41;

R41 represents a

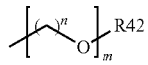

radical in which R42 represents an alkyl radical, n and m represent 2.

Very preferentially, a subject of the invention is a compound as defined above in which n4 represents 0 or 1 and R4 represents a hydrogen atom, or an alkyl radical.

Very preferentially also, a subject of the invention is a compound as defined above in which n4 represents 0 and R4 represents an alkyl radical.

Yet more preferentially, a subject of the invention is a compound as defined above in which the alkyl radical represents the methyl radical.

A subject of the present invention is also an octapeptide compound of general formula (I)

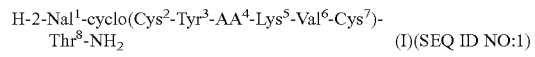

in which AA⁴ represents an amino acid of formula

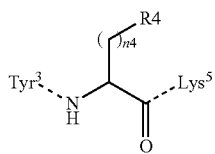

in which n4 represents an integer from 0 to 3 and R4 represents a hydrogen atom, an alkyl, aryl or heteroaryl radical, the aryl and heteroaryl radicals being optionally substituted by one or more identical or different radicals chosen from halo, nitro, hydroxy, aryl, OR41;

R41 represents a

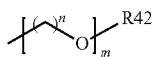

radical in which R42 represents an alkyl radical or a hydrogen atom, n is an integer from 2 to 4, and m is an integer from 1 to 4;

it being understood that all the amino acids can be of D or L configuration, with the exception of the compounds H-D-2-Nal¹-cyclo(Cys²-Tyr³-β-(3-pyridyl)-D-Ala⁴-Lys⁵-Val⁶-Cys⁷)-Thr⁸-NH₂, H-D-2-Nal¹-cyclo-Tyr³-D-Phe⁴-Lys⁵-Val⁶-Cys⁷)-Thr⁸-NH₂, H-D-2-Nal¹-cyclo(Cys²-Tyr³-D-Trp⁴-Lys⁵-Val⁶-Cys⁷)-Thr⁸-NH₂ and their salts, or a pharmaceutically acceptable salt of this compound.

Preferentially, a more particular subject of the invention is a compound as defined above in which n4 represents an integer from 0 to 2 and R4 represents an alkyl, aryl or heteroaryl radical, the aryl and heteroaryl radicals being optionally substituted by one or more identical or different radicals chosen from halo, nitro, hydroxy, aryl, OR41; and R41 represents a

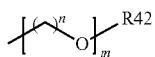

radical in which R42 represents an alkyl radical, n and m represent 2.

Preferentially a subject of the invention is a compound as defined above in which the term aryl represents a radical chosen from phenyl, naphthyl, anthryl and fluorenyl.

Preferentially a subject of the invention is also a compound as defined above in which the term heteroaryl represents a radical chosen from pyridinyl, pyrimidinyl, furyl, thienyl, benzothienyl, oxazolyl, benzoxazolyl, isoxazolyl, thiazolyl, pyrolyl, pyrazolyl, imidazolyl, triazolyl, tetrazolyl and even more preferentially, chosen from thienyl, benzothienyl and imidazolyl.

Similarly, preferentially a subject of the invention is also a compound as defined above in which the term alkyl represents a radical chosen from methyl, ethyl, propyl, isopropyl, butyl, isobutyl, tert-butyl.

Similarly, preferentially a subject of the invention is a compound as defined above in which the term alkyl represents a radical chosen from methyl, ethyl, propyl, isopropyl, butyl, isobutyl, tert-butyl; and the term cycloalkyl represents a cyclohexyl radical.

More preferentially, the invention relates to an octapeptide compound of general formula (I) in which AA⁴ represents the radical of an amino acid chosen from Trp, Ala, β-(3-benzothienyl)-Ala, β-(2-thienyl)-Ala, β-(9-anthryl)-Ala, β-(2-fluorenyl)-Ala, His, Val, 1-Nal, 2-Nal, phenyl-Gly, Homo-Phe, p-Br-Phe, p-F-Phe, m-F-Phe, o-F-Phe, m-Br-Phe, o-Br-Phe, p-NO₂-Phe, 3,5-difluoro-Phe, 4-phenyl-Phe, Tyr, p-(2-(2-methoxyethoxy)ethoxy)-Phe; β-(cyclohexyl)-Ala, p-phenylazo-Phe.

More preferentially also, the invention relates to an octapeptide compound of general formula (I) in which AA⁴ represents an amino acid chosen from Trp, Ala, β-(3-benzothienyl)-Ala, β-(2-thienyl)-Ala, β-(9-anthryl)-Ala, β-(2-fluorenyl)-Ala, His, Val, 1-Nal, 2-Nal, phenyl-Gly, Homo-Phe, p-Br-Phe, p-F-Phe, m-F-Phe, o-F-Phe, m-Br-Phe, o-Br-Phe, p-NO₂-Phe, 3,5-difluoro-Phe, 4-phenyl-Phe, Tyr, p-(2-(2-methoxyethoxy)ethoxy)-Phe.

Even more preferentially, the invention relates to an octapeptide compound of general formula (I) in which the amino acid radical AA⁴ is of D configuration and even more preferentially the amino acids 2-Nal⁷ and AA⁴ are of D configuration, the other amino acids being of L configuration.

Very preferentially also, the invention relates to an octapeptide compound of general formula (I) in which the amino acid radical AA⁴ is of L configuration and even more preferentially the amino acids 2-Nal⁷ and AA⁴ are of L configuration, the other amino acids being of D configuration.

Even more preferentially, the invention relates to an octapeptide compound of general formula (I) in which AA⁴ represents the radical of the amino acid Ala.

Preferentially, the compound according to the invention is chosen from:

H-D-2-Nal¹-cyclo(Cys²-Tyr³-β-(3-benzothienyl)-D-Ala⁴-Lys⁵-Val⁶-Cys⁷)-Thr⁸-NH₂

H-D-2-Nal¹-cyclo(Cys²-Tyr³-β-(2-thienyl)-D-Ala⁴-Lys⁵-Val⁶-Cys⁷)-Thr⁸-NH₂

H-D-2-Nal¹-cyclo(Cys²-Tyr³-D-His⁴-Lys⁵-Val⁶-Cys⁷)-Thr⁸-NH₂

H-D-2-Nal¹-cyclo(Cys²-Tyr³-D-Ala⁴-Lys⁵-Val⁶-Cys⁷)-Thr⁸-NH₂

H-D-2-Nal¹-cyclo(Cys²-Tyr³-D-Val⁴-Lys⁵-Val⁶-Cys⁷)-Thr⁸-NH₂

H-D-2-Nal¹-cyclo(Cys²-Tyr³-β-(1-naphthyl)-D-Ala⁴-Lys⁵-Val⁶-Cys⁷)-Thr⁸-NH₂

H-D-2-Nal¹-cyclo(Cys²-Tyr³-β-(2-naphthyl)-D-Ala⁴-Lys⁵-Val⁶-Cys⁷)-Thr⁸-NH₂

H-D-2-Nal¹-cyclo(Cys²-Tyr³-β-(9-anthryl)-D-Ala⁴-Lys⁵-Val⁶-Cys⁷)-Thr⁸-NH₂

H-D-2-Nal¹-cyclo(Cys²-Tyr³-β-(2-fluorenyl)-D-Ala⁴-Lys⁵-Val⁶-Cys⁷)-Thr⁸-NH₂

H-D-2-Nal¹-cyclo(Cys²-Tyr³-Ph-D-Gly⁴-Lys⁵-Val⁶-Cys⁷)-Thr⁸-NH₂

H-D-2-Nal¹-cyclo(Cys²Tyr³-homo-D-Phe⁴-Lys⁵-Val⁶Cys⁷)-Thr⁸-NH₂

H-D-2-Nal¹-cyclo(Cys²-Tyr³-p-Br-D-Phe⁴-Lys⁵-Val⁶-Cys⁷)-Thr⁸-NH₂

H-D-2-Nal¹-cyclo(Cys²-Tyr³-p-F-D-Phe⁴-Lys⁵-Val⁶-Cys⁷)-Thr⁸-NH₂

H-D-2-Nal¹-cyclo(Cys²-Tyr³-D-Tyr⁴-Lys⁵-Val⁶-Cys⁷)-Thr⁸-NH₂

H-D-2-Nal¹-cyclo(Cys²-Tyr³-m-F-D-Phe⁴-Lys⁵-Val⁶-Cys⁷)-Thr⁸-NH₂

H-D-2-Nal¹-cyclo(Cys²-Tyr³-o-F-D-Phe⁴-Lys⁵-Val⁶-Cys⁷)-Thr⁸-NH₂

H-D-2-Nal¹-cyclo(Cys²-Tyr³-3,5-diF-D-Phe⁴-Lys⁵-Val⁶-Cys⁷)-Thr⁸-NH₂

H-D-2-Nal¹-cyclo(Cys²-Tyr³-m-Br-D-Phe⁴-Lys⁵-Val⁶-Cys⁷)-Thr⁸-NH₂

H-D-2-Nal$^1$-cyclo(Cys$^2$-Tyr$^3$-o-Br-D-Phe$^4$-Lys$^5$-Val$^6$-Cys$^7$)-Thr$^8$-NH$_2$
H-D-2-Nal$^1$-cyclo(Cys$^2$-Tyr$^3$-p-Nitro-D-Phe$^4$-Lys$^5$-Val$^6$-Cys$^7$)-Thr$^8$-NH$_2$
H-D-2-Nal$^1$-cyclo(Cys$^2$-Tyr$^3$-p-Ph-D-Phe$^4$-Lys$^5$-Val$^6$-Cys$^7$)-Thr$^8$-NH$_2$
H-D-2-Nal$^1$-cyclo(Cys$^2$-Tyr$^3$-p-(2-(2-methoxyethoxy)ethoxy)-D-Phe$^4$-Lys$^5$-Val$^6$-Cys$^7$)-Thr$^8$-NH$_2$
H-2-Nal$^1$-cyclo(D-Cys$^2$-D-Tyr$^3$-Trp$^4$-D-Lys$^5$-D-Val$^6$-D-Cys$^7$)-D-Thr$^8$-NH$_2$
H-D-2-Nal$^1$-cyclo(Cys$^2$-Tyr$^3$-β-(cyclohexyl)-D-Ala$^4$-Lys$^5$-Val$^6$-Cys$^7$)-Thr$^8$-NH$_2$
H-D-2-Nal$^1$-cyclo(Cys$^2$-Tyr$^3$-p-phenylazo-D-Phe$^4$-Lys$^5$-Val$^6$-Cys$^7$)-Thr$^8$-NH$_2$
or a pharmaceutically acceptable salt of this compound.

More preferentially, the compound according to the invention as defined above is chosen from:
H-D-2-Nal$^1$-cyclo(Cys$^2$-Tyr$^3$-β-(3-benzothienyl)-D-Ala$^4$-Lys$^5$-Val$^6$-Cys$^7$)-Thr$^8$-NH$_2$
H-D-2-Nal$^1$-cyclo(Cys$^2$-Tyr$^3$-β-(2-thienyl)-D-Ala$^4$-Lys$^5$-Val$^6$-Cys$^7$)-Thr$^8$-NH$_2$
H-D-2-Nal$^1$-cyclo(Cys$^2$-Tyr$^3$-D-His$^4$-Lys$^5$-Val$^6$-Cys$^7$)-Thr$^8$-NH$_2$
H-D-2-Nal$^1$-cyclo(Cys$^2$-Tyr$^3$-β-(1-naphthyl)-D-Ala$^4$-Lys$^5$-Val$^6$-Cys$^7$)-Thr$^8$-NH$_2$
H-D-2-Nal$^1$-cyclo(Cys$^2$-Tyr$^3$-β-(2-fluorenyl)-D-Ala$^4$-Lys$^5$-Val$^6$-Cys$^7$)-Thr$^8$-NH$_2$
H-D-2-Nal$^1$-cyclo(Cys$^2$Tyr$^3$-p-Br-D-Phe$^4$-Lys$^5$-Val$^6$Cys$^7$)-Thr$^8$-NH$_2$
H-D-2-Nal$^1$-cyclo(Cys$^2$-Tyr$^3$-p-F-D-Phe$^4$-Lys$^5$-Val$^6$-Cys$^7$)-Thr$^8$-NH$_2$
H-D-2-Nal$^1$-cyclo(Cys$^2$-Tyr$^3$-D-Tyr$^4$-Lys$^5$-Val$^6$-Cys$^7$)-Thr$^8$-NH$_2$
H-D-2-Nal$^1$-cyclo(Cys$^2$-Tyr$^3$-m-F-D-Phe$^4$-Lys$^5$-Val$^6$-Cys$^7$)-Thr$^8$-NH$_2$
H-D-2-Nal$^1$-cyclo(Cys$^2$-Tyr$^3$-o-F-D-Phe$^4$-Lys$^5$-Val$^6$-Cys$^7$)-Thr$^8$-NH$_2$
H-D-2-Nal$^1$-cyclo(Cys$^2$-Tyr$^3$-3,5-diF-D-Phe$^4$-Lys$^5$-Val$^6$-Cys$^7$)-Thr$^8$-NH$_2$
H-D-2-Nal$^1$-cyclo(Cys$^2$-Tyr$^3$-m-Br-D-Phe$^4$-Lys$^5$-Val$^6$-Cys$^7$)-Thr$^8$-NH$_2$
H-D-2-Nal$^1$-cyclo(Cys$^2$-Tyr$^3$-p-Nitro-D-Phe$^4$-Lys$^5$-Val$^6$-Cys$^7$)-Thr$^8$-NH$_2$
H-D-2-Nal$^1$-cyclo(Cys$^2$-Tyr$^3$-p-(2-(2-methoxyethoxy)ethoxy)-D-Phe$^4$-Lys$^5$-Val$^6$-Cys$^7$)-Thr$^8$-NH$_2$
H-D-2-Nal$^1$-cyclo(Cys$^2$-Tyr$^3$-p-phenylazo-D-Phe$^4$-Lys$^5$-Val$^6$-Cys$^7$)-Thr$^8$-NH$_2$.

More preferentially also, the compound according to the invention as defined above is chosen from:
H-D-2-Nal$^1$-cyclo(Cys$^2$-Tyr$^3$-D-Ala$^4$-Lys$^5$-Val$^6$Cys$^7$)-Thr$^8$-NH$_2$
H-D-2-Nal$^1$-cyclo(Cys$^2$-Tyr$^3$-Ph-D-Gly$^4$-Lys$^5$-Val$^6$Cys$^7$)-Thr$^8$-NH$_2$
H-D-2-Nal$^1$-cyclo(Cys$^2$-Tyr$^3$-β-(cyclohexyl)-D-Ala $^4$-Lys$^5$-Val$^6$-Cys$^7$)-Thr$^8$-NH$_2$.

Preferentially also, the compound according to the invention as defined above is chosen from:
H-D-2-Nal$^1$-cyclo(Cys$^2$-Tyr$^3$-D-Val$^4$-Lys$^5$-Val$^6$Cys$^7$)-Thr$^8$-NH$_2$
H-D-2-Nal$^1$-cyclo(Cys$^2$-Tyr$^3$-β-(2-naphthyl)-D-Ala$^4$-Lys$^5$-Val$^6$-Cys$^7$)-Thr$^8$-NH$_2$
H-D-2-Nal$^1$-cyclo(Cys$^2$-Tyr$^3$-β-(9-anthryl)-D-Ala$^4$-Lys$^5$-Val$^6$-Cys$^7$)-Thr$^8$-NH$_2$
H-D-2-Nal$^1$-cyclo(Cys$^2$-Tyr$^3$-homo-D-Phe$^4$-Lys$^5$-Val$^6$Cys$^7$)-Thr$^8$-NH$_2$
H-D-2-Nal$^1$-cyclo(Cys$^2$-Tyr$^3$-p-Ph-D-Phe$^4$-Lys$^5$-Val$^6$Cys$^7$)-Thr$^8$-NH$_2$.

Very preferentially also, the compound according to the invention as defined above is the following compound:
H-D-2-Nal$^1$-cyclo(Cys$^2$-Tyr$^3$-D-Ala$^4$-Lys$^5$-Val$^6$Cys$^7$)-Thr$^8$-NH$_2$.

A subject of the invention is also a medicament comprising a compound according to the invention as defined previously.

A subject of the invention is also a pharmaceutical composition comprising a compound according to the invention as defined previously and more particularly when the compound is used as active ingredient.

A subject of the invention is also a therapeutic composition comprising a compound of general formula (I) as defined previously, as active ingredient in combination with at least one pharmaceutically acceptable excipient.

A subject of the invention is also a therapeutic composition comprising a compound of general formula (I) as defined previously, as pharmaceutically acceptable excipient in combination with at least one active ingredient.

Also, a subject of the invention is an immediate, controlled, sustained or delayed release therapeutic composition comprising a compound of general formula (I) as defined previously, as pharmaceutically acceptable excipient in combination with at least one active ingredient.

A subject of the invention is also a use of an octapeptide compound of general formula (I) as defined previously in order to produce a medicament.

A subject of the invention is also a use as defined above in which the medicament is intended to treat a pathology chosen from the diseases related to the growth hormone.

Finally the invention relates to the use of a compound as defined previously in order to produce a medicament; and preferentially a medicament intended to treat the pathologies in which a (or more) of the somatostatin receptor(s) is (are) involved, such as acromegalia, treatment of neuroendocrine tumours, diabetic retinopathy, treatment of the vessels, joints and skin; and preferentially acromegalia or treatment of neuroendocrine tumours.

The therapeutic composition according to the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The therapeutic composition according to the invention can also be presented in liquid form, for example, solutions, emulsions, suspensions or syrups. Appropriate liquid supports can be, for example, water, organic solvents such as glycerol or the glycols, as well as mixtures thereof, in varying proportions, in water.

The administration of a composition according to the invention can be carried out by topical, oral, parenteral route, by intramuscular, sub-cutaneous injection etc.

Unless they are defined otherwise, all the technical and scientific terms used the present Application have the same meaning as that usually understood by an ordinary specialist in the field to which this invention belongs.

The following experimental part is presented in order to illustrate the above procedures and should in no event be considered as a limit to the scope of the invention.

EXPERIMENTAL PART

1. Description of the Syntheses 1.1 Materiel Used

HPLC-MS:

The system is a Waters (2525) brand with an in-line degasser and an automated injection system (2767). The elution consists of a water and acetonitrile gradient, with 0.1% formic acid. Detection of the eluted species is carried out with a diode array (2996), an evaporative light scattering detector (ELSD) and a mass spectrometer (see hereafter). The column is of reversed-phase type, C18-grafted, model X-Bridge 100×4.6 mm with a particle size of 3.5 µm and a pore size of 13.5 nm. The flow rate is adjusted to 1 ml min-1 and the injection volume to 20 µl.

The mass spectrometer of is a Waters brand Micromass ZQ. The ionization is carried out by electrospray, with a source temperature of 120° C. and a cone voltage of 20 V. The sample is introduced continuously at 0.3 ml min-1. The analyzer is of quadrupole type (model ZQ2000).

The spectra are recorded using Mass Lynx 4.0 software in the range of m/z 100-1000 for the organic molecules and 100-2000 for the peptides.

Preparative HPLC:

Two systems are used for the purification of peptides. The system previously described equipped with a reversed phase-type column, 018-grafted, model X-Bridge 150×19 mm with a particle size of 5 µm and a pore size of 13.5 nm. The flow rate is 17 ml min-1. The second system is a Waters 2545 which is similar to the previous one, not equipped with a mass spectrometer. The column is a Thermo Hypurity, of reversed-phase type (018-grafted) of size 21.2×250 mm. It is eluted by a mixture of water and acetonitrile with 0.1% TFA at a flow rate of 20 ml min-1. The two preparative HPLC systems are used in isocratic mode after determination of the optimum conditions.

NMR Analyses:

The Nuclear Magnetic Resonance Analyses are carried out on a Bruker Advance 400

Ultrashield spectrometer. The analysis frequencies are 400 MHz for the proton, 376.4 MHz for fluorine 19 and 100 MHz for carbon 13. The NMR spectra of fluorine are recorded with a sequence of a single pulse of 90 ° and a duration of 19.5 ps. The window size is 7.5 kHz, the relaxation time 2 s and the acquisition time 0.87 s. Sixteen scans are carried out for each analysis. The spectra are recorded at ambient temperature, the chemical shifts are expressed in ppm and the coupling constants in Hz. The multiplicity is given in the following way: s=singulet, bs=broad singulet, d=doublet, bd=broad doublet, dd=doublet of doublets, ddd=doublet of doublets of doublets, t=triplet, bt=broad triplet, q=quadruplet, dq=doublet of quadruplet, m=multiplet.

HRMS Analyses:

The exact mass measurements were carried out on a time-of-flight mass spectrometer (LCT from Micromass®, UK), provided with an electrospray source (Z-spray) in positive mode. The external reference allowing the exact mass measurement is introduced in parallel with the sample and continuously (Lockspray™ configuration). The one used here is Leucine Enkephalin which produces an [M+Na]+ion at m/z=578.2591. The resolution of this device is 6500 and the results are given with a deviation from the theoretical mass of less than 5 mDa. The device is driven by the Masslynx 4.0® software. The sample solubilized in water is injected into a 50% water-50% methanol flow via an HPLC provided with an automatic sample changer (Alliance 2795 from Waters®, UK) at a flow arte of 200 pl min-1. The injection volume is 10 pl. The voltage of the capillary is 2800 V. The cone voltage is 40 V. The source temperature is 120° C. The desolvation temperature is 250° C. The flow rate of the desolvation gas (nitrogen) is 500 l h-1. The flow rate of the cone gas (nitrogen) is 20 l h-1. TDC Stop: 100 mV IR Spectrometry:

The infrared spectra of the peptides are recorded by attenuated total reflection and by Fourier transform. The device is a Bruker IFS 66 equipped with a 45° N Znse ATR module, continuously purged with nitrogen. 10 µL of solution are deposited on the crystal and thirty scans are averaged at a resolution of 4 cm-1. The signal from water is subtracted from the raw spectrum using the OPUS 4.2 software.

Freeze-dryer:

The freeze-dryer used is a Christ Alpha 2-4 LD plus connected to a vane pump making it possible to achieve vacuums of approximately 15 µbar. The aqueous samples are solidified in the liquid nitrogen before being connected to this device.

Microscopy:

TEM of Phillips CM-20 type microscope operating at 200 kV, and SEM of Leo-Gemini type, field emission gun.

1.2 Reagents Used

The synthetic peptide resin is obtained from Novabiochem, a division of Merck Biosciences (Schwalbach, Germany). The ion exchange resin comes from the Bio-Rad laboratories (Hercules, United States).

The water used is double deionized by using a Milli-Q Plus exchange system from Millipore (Billerica, United States). The solvents for the syntheses and for the purifications are purchased from Aldrich and VWR (West Chester, United States) and, unless otherwise mentioned, are used without purification.

The amino acids are purchased from Bachem (Weil am Rhein, Germany), Fluka (Buchs, Switzerland), Acros Organics (Geel, Belgium) and NeoMPS (Strasbourg, France).

Amino Acid Precursors Which Are Commercially Available:

Fmoc-L-Cys(Trt)-OH, Fmoc-L-Tyr(tBu)-OH, Fmoc-L-Lys(Boc)-OH, Fmoc-L-Val-OH, Fmoc-L-Thr(tBu)-OH, Boc-β-(2-naphthyl)-D-Ala-OH; Fmoc-β-(3-benzothienyl)-D-Ala-OH, Fmoc-β-(2-thienyl)-D-Ala-OH, Fmoc-D-His(Boc)-OH, Fmoc-D-Ala-OH, Fmoc-D-Val-OH, Fmoc-β-(1-naphthyl)-D-Ala-OH, Fmoc-β-(2-naphthyl)-D-Ala-OH, Fmoc-β-(9-anthryl)-D-Ala-OH, Fmoc-Ph-D-Gly-OH, Fmoc-homo-D-Phe-OH, Fmoc-p-Br-D-Phe-OH, Fmoc-p-F-D-Phe-OH, Fmoc-D-Tyr(tBu)-OH, Fmoc-m-F-D-Phe-OH, Fmoc-o-F-D-Phe-OH, Fmoc-3,5-diF-D-Phe-OH, Fmoc-m-Br-D-Phe-OH, Fmoc-o-Br-D-Phe-OH, Fmoc-p-Nitro-D-Phe-OH, Fmoc-p-Ph-D-Phe-OH; Fmoc-β-(cyclohexyl)-D-Ala-OH;

Fmoc-β-(2-naphthyl)-L-Ala-OH, Fmoc-D-Cys(Trt)-OH, Fmoc-L-Trp(Boc)-OH, Fmoc-D-Lys(Boc)-OH, Fmoc-D-Thr(tBu)-OH.

Synthesis of the Amino Acid Fmoc-β-(2-fluorenyl)-D-Ala-OH a/ methyl 2-(benzyloxycarbonylamino)-3-(9H-fluoren-2-yl)acrylate 1,8-diazabicyclo[5.4.0]undec-7-ene (DBU, 1.35 ml, 1.5 eq) is added at 0° C. to a solution of methyl 2-(benzyloxycarbonylamino)-2-(dimethoxyphosphoryl) acetate (2 g, 6.04 mmol, 1 eq) in dichloromethane (60 ml). After stirring for 5 min 9H-fluorene-2-carbaldehyde (1.17 mg, 6.04 mmol, 1 eq) is added. The mixture is left for 2 h at 0° C. under stirring, then the ice bath is removed, allowing the temperature to rise to a temperature comprised between 20 and 30° C.

The reaction is left under stirring for 2 h. 40 mL of dichloromethane are added to the reaction medium and after washing with 0.5 M HCl, the organic phase is dried with sodium sulphate, then evaporated. Trituration is carried out using cold diethyl ether. The supernatant is recovered and the operation is carried out several times. The solid obtained is purified on silica gel (Eluent: Hexane-AcOEt 75:25) in order to obtain 1.75 g of pure product (unknown configuration) Yield=74%. The other isomer is also recovered. The ratio of the two isomers is 95/5.

1H-NMR (CDCl$_3$): δ 3.84 (m, 2H, fluorene+3H methyl); 5.13 (s, 2H, benzyl); 7.25-7.40 (m, 7H), 7.45 (s, 1H); 7.55 (d, J=7.6, 2H); 7.72 (m, 2H), 7.79 (d, J=7.6, 1H).

13C-NMR (CDCl$_3$): δ 36.95; 52.76; 67.63; 120.04; 120.44; 123.36; 125.22; 127.04; 127.52; 128.38, 128.59; 129.17; 132.16; 132.73; 136.07; 141.04; 143.31; 143.52; 144.0; 166.02.

MS (ESI): m/z 400.0 [M+H]+

IR: λ. (cm-1): 3262, 3034, 2951 (CH alkyl), 1725 (CO), 1699. 1509, 1234, 730.

Melting point: 109° C.

b/ methyl (R)-2-(benzyloxycarbonylamino)-3-(9H-fluoren-2-yl)propanoate

The asymmetrical rhodium catalyst (35 mg, 2% mol) is added to a solution of methyl 2-(benzyloxycarbonylamino)-3-(9H-fluoren-2-yl)acrylate (1 g, 2.51 mmol) in MeOH (150 ml) in a closed metal reactor. The medium is purged of its air and put under a hydrogen atmosphere (50 bars). After 24 h, the medium is concentrated in order to quantitatively produce the reduction product.

1H-NMR (CDCl3): δ 3.15 (dd, J=14.0, J=6.4, 1H); 3.22 (dd, J=14.0, J=6.0, 1H); 3.73 (s, 3H methyl); 3.85 (s, 2H fluorene); 4.70 (m, 1H); 5.07 (d, J=12.4, 1H benzyl); 5.12 (d, J=12.4, 1H, benzyl); 5.25 (1H, NH); 7.11 (d, J=7.6, 1H); 7.27-7.38 (m, 8H); 7.53 (d, J=7.6, 2H); 7.58 (d, J=7.8, 1H); 7.75 (d, J=7.6, 1H).

13C-NMR (CDCl3): δ 36.74; 38.38; 52.27; 54.95; 66.91; 119.76; 119.85; 124.96; 125.87; 126.64, 126.70; 127.79; 128.04; 128.11; 128.45; 134.14; 136.17; 140.74; 141.27; 143.12; 143.64; 155.58, 172.01.

MS (ESI) m/z: 402.0 [M+H]+

IR: λ. (cm-1): 3347, 3025. 2949 (CH alkyl), 1741 (CO), 1689, 1523, 1256, 1024, 740

Melting point: 125° C.

Enantiomeric excess determined by chiral HPLC: 93.4% c/ (R)-2-(benzyloxycarbonylamino)-3-(9H-fluoren-2-yl propanoic acid

A solution of LiOH 96 mg in water (15 ml) is added to a solution of methyl (R)-2-(benzyloxycarbonylamino)-3-(9H-fluoren-2-yl)propanoate (800 mg, 1.99 mmol) in dioxane (35 ml) at 0° C. The reaction is followed by TLC (hexane-AcOEt 1:1) (the acid formed does not migrate). The reaction is terminated after one hour. The medium is acidified by 2 M HCl and the product is extracted with ethyl acetate. The product is recovered quantitatively (735 mg) after drying with sodium sulphate, evaporation under vacuum and crystallization from ether.

1H-NMR ((CD$_3$) δ 2.90 (dd, J=14.0, J=9.6, 1H); 3.20 (dd, J=13.6, J=4.8, 1H); 3.71 (s, 2H, fluorene); 4.40 (dd, J=9.6, J=4.8, 1H); 4.87 (d, J=12.6, 1H benzyl); 4.96 (d, J=12.6, 1H, benzyl); 7.12 (m, 6H); 7.18 (t, J=7.6, 1H); 7.26 (t, J=7.6, 1H); 7.32 (s, 1H); 7.43 (d, J=7.6, 1H); 7.60 (d, J=7.6, 1H); 7.68 (d, J=7.8, 1H).

13C-NMR ((CD$_3$) δ 36.17; 36.60; 55.68; 65.14; 119.59; 119.71; 125.01; 125.77; 126.43; 126.63; 127.40; 127.59; 127.70; 128.45; 128.15; 136.57; 136.89; 139.39; 140.90; 142.82; 142.88; 155.92; 173.27.

MS (ESI) m/z: 388 [M+H]+

IR: λ. (cm-1): 3333; 3035; 2902 (CH alkyl); 1724 (CO); 1705; 1689; 1531; 1245; 1062; 734.

Melting point: 141° C.

d/ (R)-2-amino-3-(9H-fluoren-2-yl) propanoic acid

Pd/C (65 mg) is added to a solution of (R)-2-(benzyloxycarbonylamino)-3-(9H-fluoren-2-yl)propanoic acid (650 mg, 1.68 mmol) in methanol (80 mL). The medium is purged with nitrogen then with hydrogen. The reaction is left for 6 h under vigorous stirring: a precipitate appears. The medium is filtered: a mixture of the desired product and Pd/C is recovered before solubilization in a dioxane-water mixture (1:1) then acidification with 2 M HCl so as to dissolve the amino acid. This solution is filtered, the dioxane is evaporated off under vacuum then the aqueous phase is neutralized by the addition of 2 M NaOH. After evaporation, the white powder obtained is washed with water in order to remove excess salts. 500 mg of amino acid are recovered. The yield is 85%.

MS (ESI) m/z: 254 [M+H]+

IR: λ. (cm-1): 3425; 3019; 2960 (CH alkyl); 1567; 1402; 1316; 737.

Melting point: 225° C.

UV λ. (nm): 206 (abs=0.868), 267 (abs=0.446), 303 (abs=0.203)

Fluorescence: (excitation at 267 nm) maximum at 312 nm.

Enantiomeric excess determined by Chiral HPLC: 93.4%.

e/ (R)-2-(((9H-fluoren-9-yl)methoxy)carbonylamino)-amino-3(9H-fluoren-2-yl) propanoic acid or Fmoc-β-(2-fluorenyl)-D-Ala-OH A solution of FmocOSu (820 mg, 2.43 mmol, 1.1 eq) in 20 ml of dioxane is added dropwise to a solution of the amino acid (R)-2-amino-3-(9H-fluoren-2-yl)propanoic (560 mg, 2.21 mmol, 1 eq.) in a mixture of dioxane (50 mL)-sodium carbonate at 10% in water (30 ml). The disappearance of FmocOSu is followed by TLC eluent hexane-AcOEt (1:1). The reaction medium is stirred for 3h. The reaction mixture is extracted with ethyl acetate and the organic phase is recovered and evaporated. The solid obtained is crystallized from AcOEt before filtration. 860 mg of expected product are recovered. Yield=82%.

1H-NMR ((CD$_3$)$_2$SO): δ 3.00 (dd, J=13.2, J=5.8, 1H); 3.13 (dd, J=13.2, J=4.9, 1H); 3.76 (s, 2H, fluorene); 3.81 (dd, J=6.4, J=4.8, 1H), 4.12 (dd, J=9.8, J=6.4, 1H, CHβ Fmoc); 4.19 (t, J=6.4, 1H, Fmoc); 4.30 (dd, J=9.8, J=6.4, 1H, CH'β Fmoc); 6.35 (s, 1H, NH); 7.12 (d, J=7.6, 1H); 7.20-7.40 (m, 7H); 7.53 (d, J=7.4, 1H); 7.62 (t, J=7.2, 2H); 7.67 (d, J=7.8, 1H); 7.81 (d, J=7.6, 1H); 7.7 (d, J=7.6, 2H).

13C-NMR (CD$_3$SO): the molecule is degraded.

MS (ESI) m/z: 476.0 [M+H]+

IR: λ. (cm-1): 3382. 3051; 2958 (CH alkyl); 1678; 1605; 1528. 1411; 1254; 1037; 735.

Synthesis of N-fluorenylmethoxycarbonyl-4-(2-(2-methoxyethoxy)ethoxy)-D-Phe or Fmoc-p-O-2-(2-methoxyethoxy)ethoxy-D-Phe a/ N-terbutyloxycarbonyl-4-(2-(2-methoxyethoxy)ethoxy)-D-Phe 100 mg (0.35 mmol) of Boc-D-tyrosine-OH as well as 155 mg (1.12 mmol, 3.1 eq) are introduced into 1 ml of DMF and 100 pl of H$_2$O. At 0° C., 180 μl (1.43 mmol, 4.1 eq) of 1-bromo-2-(2-methoxyethoxy)ethane is introduced and the reaction is heated at 50° C. for 7 h. The reaction medium is then dissolved in ethyl acetate and dilute hydrochloric acid is added in order to adjust the pH of the aqueous phase to 2.The organic phase is washed with dilute hydrochloric acid, then dried over magnesium sulphate. After evaporation, 218.9 mg of amorphous solid is recovered. This solid is dissolved in 2 ml of 1 M soda and 2 ml of dioxane and left under stirring for 1 h 30.The pH is adjusted to 2 with dilute hydrochloric acid, then the product is extracted with ethyl acetate. 137.7 mg of crude product is recovered. The purification is carried out by silica column with an ethyl acetate-cyclohexane-acetic acid eluent 60:40:1%. After evaporation 94.6 mg of pure product is recovered, i.e. a yield of 68%.

NMR $^1$H (400 MHz, CDCl$_3$): δ 1.41 (s, 9H, tBu); 3.01 (dd, J=13.7, J=5.7, 1H, CHβ); 3.11 (dd, J=13.7, J=4.8, 1H, CHβ); 3.39 (s, 3H, OCH$_3$); 3.55-3.60 (m, 2H, CH$_2$ ethoxy); 3.69-3.74 (m, 2H, CH$_2$ ethoxy); 3.81-3.87 (m, 2H, CH$_2$ ethoxy); 4.07-4.16 (m, 2H, CH$_2$ ethoxy); 4.50-4.59 (m, 1H CHα); 4.97 (d, J=7.7, 1H, NH); 6.84 (d, J=8.3, 2H, CHAr); 7.07 (d, J=8.3, 2H, CH Ar).

MS (ESI) m/z: 384.2 [M+H]$^+$ b/ 4-(2-(2-methoxy)ethoxy)-D-Phe 1.89 g of N-ter-butyloxycarbonyl-4-(2-(2-methoxyethoxy)ethoxy)-D-Phe is introduced into 26 ml of 35% HCl and 74 ml of ethyl acetate. The reaction is left for 3 h under stirring. After evaporation, the solid is triturated three times with diethyl ether in order to obtain 1.12 g of white solid, i.e. a yield of 66%.

NMR $^1$H ((CD$_3$)$_2$SO): δ 3.04 (d, J=6.3, 2H, CHHβ); 3.23 (s, 3H, OCH$_3$); 3.41-3.46 (m, 2H, CH$_2$ ethoxy); 3.53-3.59 (m, 2H, CH$_2$ ethoxy); 3.68-3.73 (m, 2H, CH$_2$ ethoxy); 4.01-4.06 (m, 2H, CH$_2$ ethoxy); 4.09-4.12 (m, 1H CHα); 6.89 (d, J=8.8, 1H, CH Ar); 7.16 (d, J=8.8, 1H, CH Ar).

NMR $^{13}$C ((CD$_3$)$_2$SO): δ 34.84 (Cβ); 53.17 (Cα); 58.11 (CH$_3$O); 67.16 (CH$_2$ ethoxy); 68.97 (CH$_2$ ethoxy); 68.77 (CH$_2$ ethoxy); 71.34 (CH$_2$ ethoxy); 114.57 (C meta Ar); 126.61 (C ortho ar); 130.65 (CH$_2$-$\underline{C}$ Ar); 157.84 (O—C Ar); 170.30 (CO).

MS (ESI) m/z: 284, 1 [M+H]$^+$ c/ N-fluorenylmethoxycarbonyl-4-(2-(2-methoxyethoxy)ethoxy)-D-Phe 812 mg (2.87 mmol) of 4-(2-(2-methoxyethoxy)ethoxy)-D-Phe is introduced into 4 ml of distilled water and 4 ml of acetone. 300 mg (2.83 mmol, 0.98 eq) of Na$_2$CO$_3$ and 954.6 mg (2.83 mmol, 0.98 eq) of FmocOSu are added to it. The white suspension is stirred for 5 h 30 at a temperature comprised between 20 and 30° C. The acetone is then evaporated off, the medium is adjusted to pH=2 with hydrochloric acid and the product is extracted with ethyl acetate. The organic phases are combined, washed with a saturated solution of NaCl then dried over anhydrous MgSO$_4$. After evaporation, 1.5 g of crude product is obtained. This product is purified on approximately 120 g of silica, with a dichloromethane-methanol-acetic acid eluent 98:2:5, in order to obtain 939 mg of white solid, i.e. a yield of 65%.

NMR $^1$H (CDCl$_3$): δ 3.05 (dd, J=14.0, J=5.7, 1H, CHβ); 3.13 (dd, J=14.0, J=5.4, 1H, CH'β); 3.38 (s, 3H, OCH$_3$); 3.55-3.59 (m, 2H, CH$_2$ ethoxy); 3.67-3.72 (m, 2H, CH$_2$ ethoxy); 3.80-3.85 (m, 2H, CH$_2$ ethoxy); 4.04-4.10 (m, 2H, CH$_2$ ethoxy); 4.20 (t, J=6.8, 1H, CH); 4.34 (dd, J=10.8, J=6.8, 1H, CHβ Fmoc); 4.44 (dd, J=10.8, J=6.8, 1H, CH'β Fmoc); 4.63 (dd, J=14.0, J=5.7, 1H, CHα); 5.30 (s, 1H, NH); 6.81 (d, J=8.1, 2H, CH ar,); 7.03 (d, J=8.1, 2H, CHAr,); 7.30 (t, J=7.4, 2H, fluorenyl); 7.40 (t, J=7.4, 2H, fluorenyl); 7.56 (t, J=5.8, 2H, fluorenyl); 7.76 (d, J=7.4, fluorenyl).

NMR $^{13}$C (CDCl$_3$): δ 36.89 (CH$_2$β); 47.08 (CH Fmoc); 54.66 (CHa); 58.96 (CH$_3$O); 66.96 (CH$_2$ Fmoc); 67.22 (CH$_2$ ethoxy); 69.68 (CH$_2$ ethoxy); 70.55 (CH$_2$ ethoxy); 71.83 (CH$_2$ ethoxy); 114.65 (C meta Phe,); 119.92 (CH fluorenyl); 125.01 (CH fluorenyl); 127.02 (C ortho ar); 127.67 (CH fluorenyl); 127.77 (CH fluorenyl); 130.34 (CH$_2$-$\underline{C}$ Phe,); 141.24 (C fluorenyl); 143.64 (C fluorenyl); 155.70 (CO Fmoc); 157.84 (O—C ar,); 170.30 (CO).

MS (ESI) m/z: 506.0 [M+H]$^+$

Synthesis of the Amino Acid Fmoc-β-(p-phenylazo)-D-Phe-OH 400 mg (1 mmol) of Fmoc-pNH2-D-Phe-OH and 150 mg (1.4 mmol) of nitrosobenzene are placed in 20 ml of glacial acetic acid, then the mixture is stirred at ambient temperature for 16 h. 150 mg of nitrosobenzene is then added again and stirring is continued for 24 h. The solvent is then evaporated off and the residue is crystallized from hot methanol. The mixture is then placed at +4° C. overnight and the crystals are recovered by filtration, rinsed with cold methanol (2×20 ml) then dried with a dessicator under vacuum. 300 mg of the amino acid is recovered. The yield is 61%.

NMR $^1$H (400 MHz, CD$_3$OD): δ 3.04 (dd, J=9.6, J=13.6, 1H); 3.22-3.28 (m, 1H); 4.15 (t, J=6.8, 1H); 4.24 (dd, J=6.8, J=10.4, 1H); 4.33 (dd, J=7.2, J=10.4, 1H); 4.50 (dd, J=4.4, J=9.6, 1H); 7.27 (t, J=8, 2H); 7.36 (m, 2H); 7.42 (d, J=8.4, 2H); 7.49-7.59 (m, 5H); 7.76 (d, J=7.6, 2H); 7.83 (d, J=8.4, 2H); 7.88 (dd, J=6.8, 2H);.

MS (ESI) m/z: 492.1 [M+H]$^+$ 1.3 Preparation of the Octapeptide Compounds 1.3.1 General Procedure for the Synthesis of Peptides The synthesis comprises 4 main stages as Diagram 1 shows:

Diagram 1

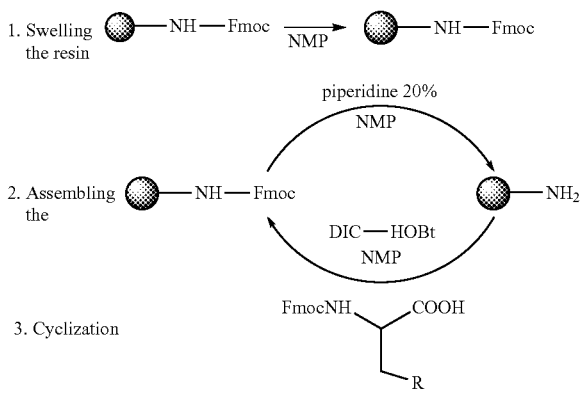

-continued
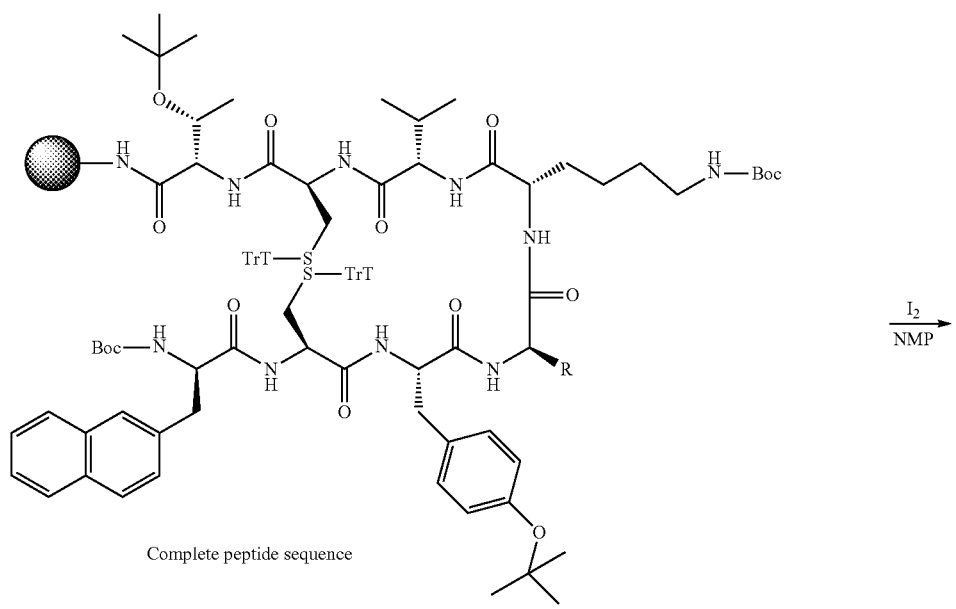
Complete peptide sequence
$\xrightarrow{I_2}{NMP}$
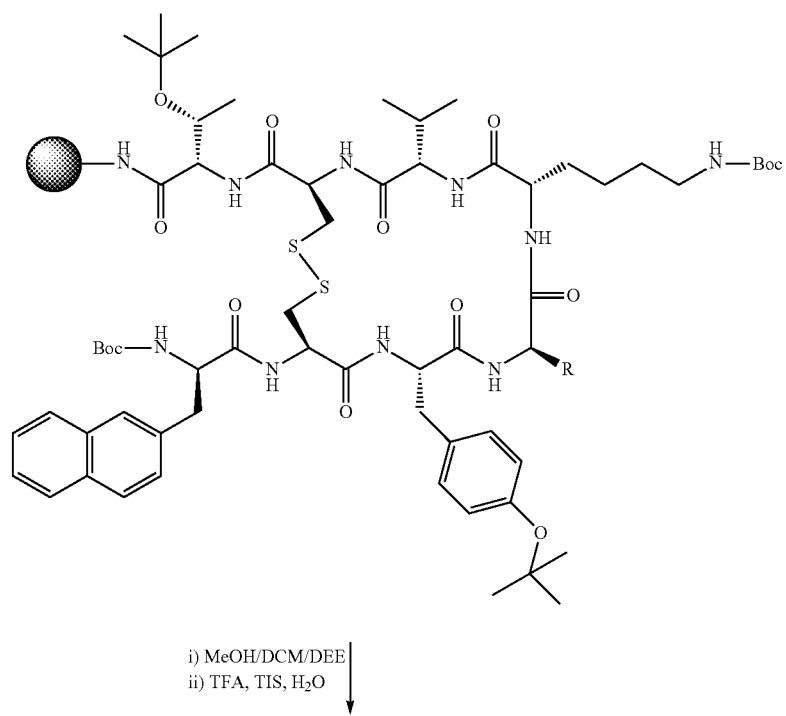
4. Cleavage
i) MeOH/DCM/DEE
ii) TFA, TIS, H$_2$O -continued Peptide in solution
(TFA salt)

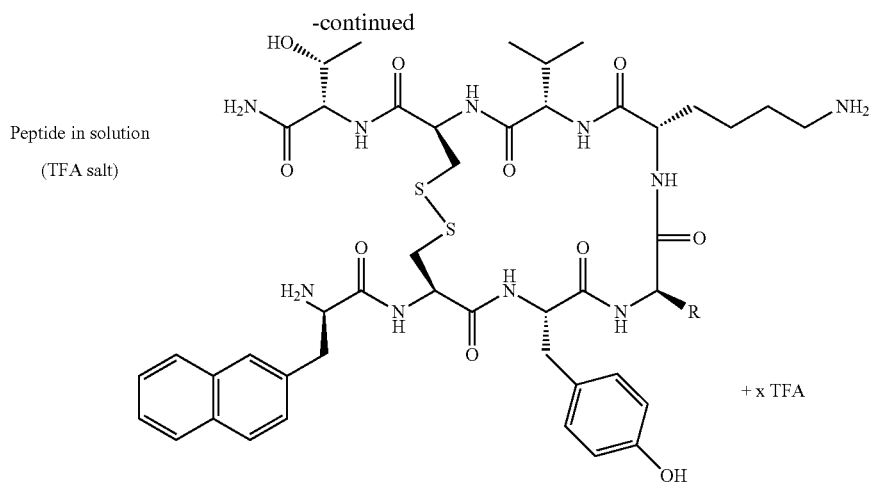

+ x TFA

1/Wetting the Resin:

The resin 4-(2',4'-dimethoxyphenyl-fluorenylmethoxycarbonyl-aminomethyl)-phenoxyacetamido-norleucyl-(4-methyl)-benzhydrylamine—polystyrene base—divinylbenzene (Rink Amide MBHA) is introduced into a syringe provided with a sintered glass, a tap at one end and a stopper at the other. It is filled with NMP and the mixture is placed under gentle stirring for 1 h. The solvent is then eliminated by filtration.

2/Coupling the Amino Acids:

The amino acids are coupled together in the desired order using a coupling reaction. The amino acid (2 eq) is introduced with 1-hydroxybenzotriazole (HOBt, 2.2 eq) and N,N'-diisopropylcarbodiimide (DIC, 2.2eq) into N-methylpyrrolidinone (NMP, 5 ml/g of resin) in a test tube and stirred for a few minutes. It is then placed in the presence of the resin in its receptacle. The reaction mixture is stirred for 1 h 30 then filtered. The double coupling technique is used: the reaction mixture is filtered when the reaction has progressed by approximately 50%, and fresh reagents are reintroduced, in order to optimize the speed of reaction and the purity of the final product. The second stage consists of deprotecting the new amino acid introduced, in order to allow a new coupling. The deprotection is carried out by three treatments with piperidine in NMP (20% v/v), 5 ml/g of resin following by three washings with NMP (10 ml/g of resin). In order to monitor the reaction, 5 µl of the filtrate corresponding to the first treatment, then 10 µl of the next two, as well as the first washing, i.e. 4 samples, are introduced into 2 ml of piperidine before measurement of the UV absorbance at 290 nm. Between each stage, three washings of the resin are carried out with NMP (10 ml/g of resin). This assembly stage therefore consists of two reactions: the coupling reaction of the amino acids and the deprotection reaction of the Fmoc group, to be carried out iteratively until the peptide sequence is complete.

3/Formation of the Disulphide Bridge:

Once the sequence is assembled, the peptide must be cyclized by the formation of the disulphide bridge. The disulphide bridge is formed by three treatments with diiodine 1 eq in NMP (5 ml/g of resin) for 2 min, 3 min and 5 min respectively. The resin is then washed 5 times with DCM and 5 times with NMP in order to eliminate the excess iodine retained in the resin (10 ml/g of resin).

4/Cleavage:

The resin must be prepared for the cleavage by two washings with NMP, two washings with methanol (MeOH), two washings with dichloromethane (DCM) and two washings with diethyl ether (DEE) (10 ml per gram of resin). The resin is then placed under vacuum for one day. The cleavage is carried out in a glass flask provided with a magnetic stirrer. The reaction mixture is formed from trifluoroacetic acid (TFA, 10 ml/g of resin) as well as triisopropylsilane (TIS) and water (3% and 2% v/v). The reaction is stirred for 4 h at ambient temperature. The medium is then filtered on sintered glass and the solid is washed twice with TFA. The filtrate is then evaporated in order to obtain a very thick white liquid. This is dissolved in a water-acetonitrile mixture 1:1 in order to be freeze-dried. After this stage, the peptide is present in the form of trifluoroacetate salt.

1.3.2 Purification

Purification is carried out by preparative high performance liquid chromatography (HPLC). The stationary phase is called "reversed" as it is grafted with $C_{18}$ alkyl chains. The mobile phase is constituted by a fixed mixture (isocratic) of water and acetonitrile with 0.1% of TFA or 1% of formic acid serving to neutralize the residual non-grafted silanols which may exist on the stationary phase.

The peptide must be dissolved in a water-acetonitrile mixture in order be injected into the preparative HPLC. A solubility study is first carried out on a small quantity. It allows the optimum percentage of acetonitrile and the maximum quantity of peptide to be established. The lowest possible percentage of acetonitrile with a very high concentration of peptide and a resultant clear solution constitute ideal conditions. By way of example, the solubility of the 4-para-fluorophenylalanine derivative (Example 13 hereafter) was established at 49 g $l^{-1}$ in a water-acetonitrile solution 58:42.

After purification, the fractions containing the purified peptide are combined and evaporated under vacuum. The pure peptide is then recovered in large quantities of solvent to be evaporated before proceeding to freeze-drying. The peptide is in general present in the form of trifluoroacetate salt which must be exchanged by an acetate before physicochemical analysis.

1.3.3 Ion Exchange

The exchange is carried out on a strong anion exchange type resin (AG1-X8 Biorad). 245 mg of this resin are firstly washed three times with 10 ml of 1.6 N acetic acid then three times with 10 ml of 0.16 M acetic acid. 20 mg of peptide as TFA salt is then introduced into 4 ml of water and the receptacle is stirred rotatively for 1 h. The liquid is then filtered and the resin washed twice with 1 ml of distilled water. The fractions are combined then lyophilized.

1.4 Examples

The products have been characterized according to the standard methods known to a person skilled in the art described previously.

Example 1

H-D-2-Nal[1]-cyclo(Cys[2]-Tyr[3]-β-(3-benzothienyl)-D-Ala[4]-Lys[5]-Val[6]-Cys[7])-Thr[8]-$NH_2$.2 $CH_3COOH$

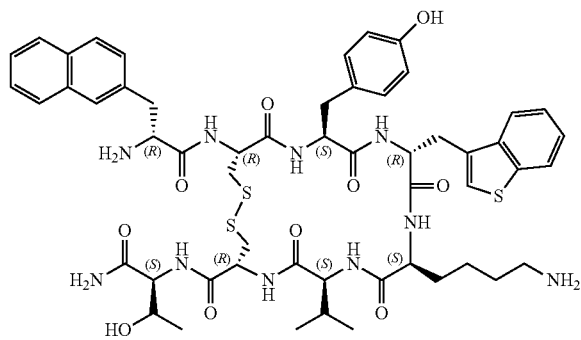

The open peptide is obtained according to the protocol described previously by successive coupling, deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-β-(3-benzothienyl)-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal[1]-cyclo(Cys[2]-Tyr[3]-β-(3-benzothienyl)-D-Ala[4]-Lys[5]-Val[6]-Cys[7])-Thr[8]-$NH_2$.2 $CH_3COOH$.

HPLC: rt=9.8 min

$^1$H NMR (400 Mhz, $D_2O$): δ 0.28-0.40 (m, 1H); 0.42-0.54 (m, 1H); 0.90 (d, J=6.6, 3H); 0.92 (d, J=6.6, 3H); 1.20 (d, J=6.4, 3H); 1.28-1.34 (m, 1H); 1.48-1.62 (m, 1H); 1.90 (s, 6H); 1.90-2.20 (m, 1H); 2.44 (dd, J=14.6, J=4.2, 1H); 2.57 (dd, J=14.8, J=9.3, 1H); 2.65-2.82 (m, 4H); 2.92 (d, J=7.4, 2H); 3.06 (dd, J=13.9, J=5.5, 1H); 3.12-3.22 (m, 1H); 3.29 (dd, J=13.3, J=9.5, 1H); 3.43 (dd, J=13.5, J=5.5, 1H); 3.81 (dd, J=10.3, J=3.7, 1H); 4.24 (dd, J=6.4, J=4.1, 1H); 4.26-4.38 (m, 3H); 4.64 (t, J=7.5, 2H); 6.84 (d, J=8.2, 2H); 7.12 (d, J=8.2, 2H); 7.31 (s, 1H); 7.38-7.50 (m, 3H); 7.54 (dd, J=9.4, J=3.8, 1H); 7.55 (dd, J=9.4, J=3.8, 1H); 7.71 (d, J=7.7, 1H); 7.78 (s, 1H); 7.85-7.90 (m, 1H); 7.90-7.95 (m, 2H); 7.98 (d, J=7.5, 1H).

HRMS ($H_2O$) m/z: 1113.4368 [M+H]+(calc. 1113.4360) C, 54; H, 69; N, 10; O, 10; S, 3

Example 2

H-D-2-Nal[1]-cyclo(Cys[2]-Tyr[3]-β-(2-thienyl)-D-Ala[4]-Lys[5]-Val[6]-Cys[7])-Thr[8]-$NH_2$.2 $CH_3COOH$

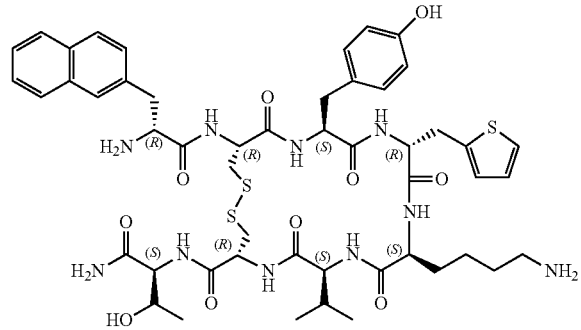

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-β-(2-thienyl)-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal[1]-cyclo(Cys[2]-Tyr[3]-β-(2-thienyl)-D-Ala[4]-Lys[5]-Val[6]-Cys[7])-Thr[8]-$NH_2$.2 $CH_3COOH$.

HPLC: rt=9.7 min

$^1$H NMR (400 Mhz, $D_2O$) δ 0.76-0.88 (m, 1H); 0.92 (d, J=6.6, 3H); 0.95 (d, J=6.6, 3H); 1.19 (d, J=6.4, 3H); 1.40-1.54 (m, 3H); 1.76-1.88 (m, 1H); 1.93 (s, 6H); 2.14-2.26 (m, 1H); 2.41 (dd, J=14.8, J=3.8, 1H); 2.63 (dd, J=15.4, J=9.7, 1H); 2.68 (dd, J=15.0, J=3.6, 1H); 2.74-2.82 (m, 1H); 2.83-2.95 (m, 4H); 3.10 (d, J=8.0, 1H); 3.37 (dd, J=13.6, J=8.6, 1H); 3.47 (dd, J=13.8, J=5.6, 1H); 4.02 (d, J=9.7, 1H); 4.07 (dd, J=10.8, J=3.5, 1H); 4.21 (dq, J=10.4, J=6.4, 1H); 4.28 (t, J=8.1, 1H); 4.31 (d, J=4.0, 1H); 4.42 (dd, J=8.6, J=6.2, 1H); 4.62 (t, J=7.4, 1H); 4.89 (dd, J=10.5, J=3.6, 1H); 4.93 (dd, J=10.5, J=3.6, 1H); 6.82 (m, 3H); 6.98 (m, 2H); 7.11 (d, J=8.4, 2H); 7.31 (d, J=5.1, 1H); 7.47 (d, J=8.2, 1H); 7.54 (dd, J=9.5, J=3.3, 1H); 7.55 (dd, J=9.5, J=3.3, 1H); 7.8 (s, 1H); 7.82-7.88 (m, 3H).

HRMS ($H_2O$) m/z: 1063.4230 [M+H]+(calc. 1063.4204) C, 50; H, 67; N, 10; O, 10; S, 3

Example 3

H-D-2-Nal[1]-cyclo(Cys[2]-Tyr[3]-D-His[4]-Lys[5]-Val[6]-Cys[7])-Thr[8]-$NH_2$.2 $CH_3COOH$

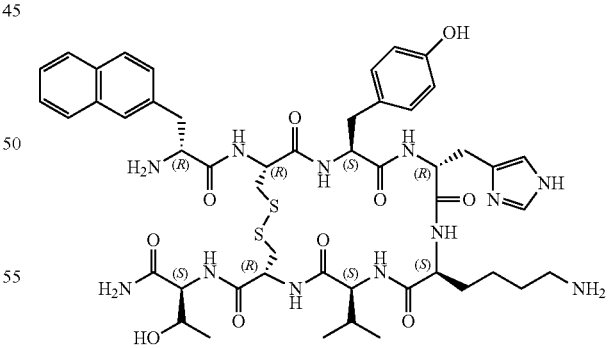

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-His-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-D-His$^4$-Lys$^5$-Val$^6$-Cys$^7$)-Thr$^8$-NH$_2$.2 CH$_3$COOH.

HPLC: rt=6.3 min $^1$H NMR (400 Mhz, D$_2$O): δ 0.90 (d, J=6.6, 3H); 0.94 (d, J=6.6, 3H); 1.02-1.14 (m, 2H); 1.17 (d, J=6.6, 3H); 1.51-1.64 (m, 3H); 1.83-1.90 (m, 1H); 1.91 (s, 6H); 2.10-2.18 (m, 1H); 2.53 (dd, J=14.6, J=4.4, 1H); 2.60 (dd, J=14.8, J=9.5, 1H); 2.70 (dd, J=14.6, J=4.4, 1H); 2.75 (dd, J=14.4, J=4.2, 1H); 2.84-2.94 (m, 5H); 2.99 (dd, J=15.2, J=7.2, 1H); 3.36 (dd, J=13.9, J=8.6, 1H); 3.46 (dd, J=13.8, J=5.7, 1H); 4.04 (d, J=9.7, 1H); 4.13-4.23 (m, 2H); 4.26-4.32 (m, 2H); 4.40 (dd, J=8.7, J=5.9, 1H); 4.55 (t, J=7.7, 1H); 4.86 (dd, J=9.6, J=4.4, 1H); 4.92 (dd, J=10.4, J=4.6, 1H); 6.74 (d, J=8.6, 2H); 7.01 (d, J=1.3, 1H); 7.04 (d, J=8.6, 2H); 7.46 (dd, J=8.5, J=1.7, 1H); 7.52 (ddd, J=6.7, J=4.4, J=1.6, 1H); 7.53 (ddd, J=6.7, J=4.4, J=1.6, 1H); 7.80 (s, 1H); 7.93-7.93 (m, 3H); 8.29 (d, J=1.1; 1H).

HRMS (H$_2$O) m/z: 1047.4507 [M+H]+(calc. 1047.4545) C, 49; H, 66; N, 12; O10; S, 2

Example 4

H-D-2-Nal$^1$-cyclo(Cys$^2$Tyr$^3$-D-Ala$^4$-Lys$^5$-Val$^6$Cys$^7$)-Thr$^8$-NH$_2$.2 CH$_3$COOH

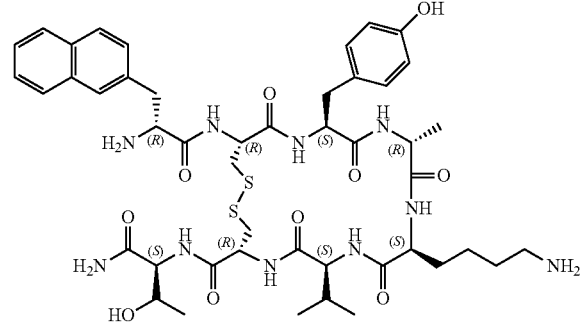

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-D-Ala$^4$-Lys$^5$-Val$^6$-Cys$^7$)-Thr$^8$-NH$_2$.2 CH$_3$COOH.

HPLC: rt=9.8 min $^1$H NMR (400 Mhz, D$_2$O): δ 0.93 (d, J=6.6, 3H); 0.96 (d, J=6.6, 3H); 1.18 (d, J=7.8, 3H); 1.20 (d, J=6.6, 3H); 1.34-1.44 (m, 2H); 1.60-1.68 (m, 2H); 1.68-1.80 (m, 2H); 1.90 (s, 6H); 1.92-2.20 (m, 1H); 2.12-2.22 (m, 1H); 2.45 (dd, J=14.6, J=4.9, 1H); 2.55 (dd, J=14.7, J=8.7, 1H); 2.74 (d, J=1.3, 1H); 2.76 (s, 1H); 2.90-3.00 (m, 4H); 3.3 (dd, J=13.5, J=9.1, 1H); 3.44 (dd, J=13.7, J=5.6, 1H); 4.04 (d, J=9.5, 1H); 4.07 (d, J=7.3, 1H); 4.2 (dd, J=9.9, J=4.1, 1H); 4.24 (dd, J=6.5, J=3.9, 1H); 4.28-4.32 (m, 1H); 4.33 (d, J=4.0, 1H); 4.55 (dd, J=7.8, J=7.3, 1H); 4.82-4.88 (m, 1H); 6.82 (d, J=8.6, 2H); 7.11 (d, J=8.6, 2H); 7.47 (dd, J=8.5, J=1.7, 1H); 7.54 (ddd, J=5.7, J=4.7, J=2.0, 1H); 7.55 (ddd, J=5.7, J=4.7, J=2.0, 1H); 7.79 (d, J=0.9, 1H); 7.86-7.96 (m, 3H).

HRMS (H$_2$O) m/z: 1003.4161 [M+Na]+(calc. 1003.4146) C, 46; H, 64; Na N, 10; O, 10; S, 2

Example 5

H-D-2-Nal$^1$-cyclo(Cys$^2$Tyr$^3$-D-Val$^4$-Lys$^5$-Val$^6$Cys$^7$)-Thr$^8$-NH$_2$.2 CH$_3$COOH

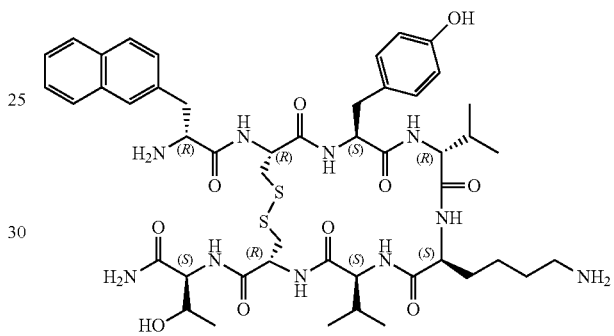

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Val-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-D-Val$^4$-Lys$^5$-Val$^6$-Cys$^7$)-Thr$^8$-NH$_2$.2 CH$_3$COOH.

HPLC: rt=10.7 min $^1$H NMR (400 Mhz, D$_2$O): δ 0.73 (d, J=6.6, 3H); 0.80 (d, J=6.8, 3H); 0.93 (d, J=6.8, 3H); 0.98 (d, J=6.6, 3H); 1.19 (d, J=6.6, 3H); 1.30-1.50 (m, 2H); 1.58-1.82 (m, 4H); 1.60-2.08 (m, 4H); 1.92 (s, 6H); 1.96-2.06 (m, 1H); 2.14-2.24 (m, 1H); 2.51 (dd, J=14.8, J=3.8, 1H); 2.62 (dd, J=14.8, J=10.0, 1H); 2.69 (dd, J=14.5, J=3.5, 1H); 2.79 (dd, J=14.9, J=11.2, 1H); 2.88-3.00 (m, 3H); 3.37 (dd, J=13.9, J=8.6, 1H); 3.57 (dd, J=13.9, J=5.8, 1H); 3.60 (d, J=9.7, 1H); 4.05 (d, J=9.7, 1H); 4.21 (dd, J=6.3, J=3.9, 1H); 4.25 (dd, J=10.7, J=3.7, 1H); 4.30 (d, J=3.8, 1H); 4.42 (dd, J=8.6, J)=5.8, 1H); 4.61 (dd, J=8.4, J=6.9, 1H); 4.95 (dd, J=9.3, J=3.6, 1H); 4.96 (dd, J=11.8, J=2.9, 1H); 6.81 (d, J=8.6, 2H); 7.12 (d, J=8.4, 2H); 7.47 (dd, J=8.4, J=1.5, 1H); 7.54 (dd, J=10.2, J=3.8, 1H); 7.55 (dd, J=10.2, J=3.8, 1H); 7.80 (s, 1H); 7.84-7.94 (m, 3H).

HRMS (H₂O) m/z: 1009.4627 [M+H]+(calc. 1009.4640) C, 48; H, 69; N, 10; O, 10; S, 2

Example 6

H-D-2-Nal¹-cyclo(Cys²Tyr³-l3-(1-naphthyl)-D-Ala⁴-Lys⁵-Val⁶-Cys⁷)-Thr⁸-NH₂.2 CH₃COOH

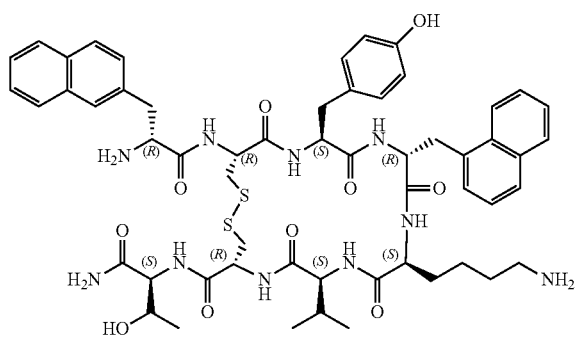

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-β-(1-naphthyl)-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-β-(1-naphthyl)-D-Ala⁴-Lys⁵-Val⁶-Cys⁷)-Thr⁸-NH₂.2 CH₃COOH.

HPLC: rt=8.9 min

¹H NMR (400 Mhz, D₂O): δ-0.10-0.10-0.04 (m, 1H); 0.22-0.34 (m, 1H); 0.87 (d, J=4.6, 3H); 0.89 (d, J=4.6, 3H); 0.98-1.10 (m, 1H); 1.18 (d, J=6.4, 3H); 1.20-1.30 (m, 1H); 1.40-1.52 (m, 1H); 1.95 (s, 6H); 2.06-2.18 (m, 1H); 2.42 (dd, J=14.9, J=3.9, 1H); 2.57 (dd, J=14.9, J=8.8, 1H); 2.64 (t, J=8.0, 2H); 2.72 (dd, J=14.8, J=4.8, 1H); 2.78 (dd, J=10.8, J=4.8, 1H); 2.89 (dd, J=13.3, J=8.3, 1H); 2.89 (dd, J=13.6, J=6.8, 1H); 3.26 (d, J=8.4, 2H); 3.34 (dd, J=13.4, J=9.0, 1H); 3.48 (dd, J=13.7, J=6.0, 1H); 3.68 (dd, J=10.8, J=3.7, 1H); 3.90 (d, J=9.7, 1H); 4.21 (ddd, J=12.7, J=6.4, J=4.0, 1H); 4.29 (d, J=3.8, 1H); 4.31 (t, J=8.6, 1H); 4.42 (dd, J=8.7, J=5.8, 1H); 4.66 (dd, J=8.5, J=6.8, 1H); 4.82-4.87 (m, 1H); 6.86 (d, J=8.6, 2H); 7.14 (d, J=8.6, 2H); 7.28 (d, J=7.3, 1H); 7.45 (t, J=7.7, 1H); 7.46 (d, J=9.7, 1H); 7.53 (dd, J=6.4, J=3.5, 1H); 7.54 (dd, J=6.4, J=3.5, 1H); 7.57-7.65 (m, 2H); 7.78 (s, 1H); 7.84-7.97 (m, 6H).

HRMS (H₂O) m/z: 1129.4578 [M+Na]+(calc. 1129.4516) C, 56; H, 70; Na N, 10; O, 10; S, 2

Example 7

H-D-2-Nal¹-cyclo(Cys²-Tyr³-β-(2-naphthyl)-D-Ala⁴-Lys⁵-Val⁶-Cys⁷)-Thr⁸-NH₂.2 CH₃COOH

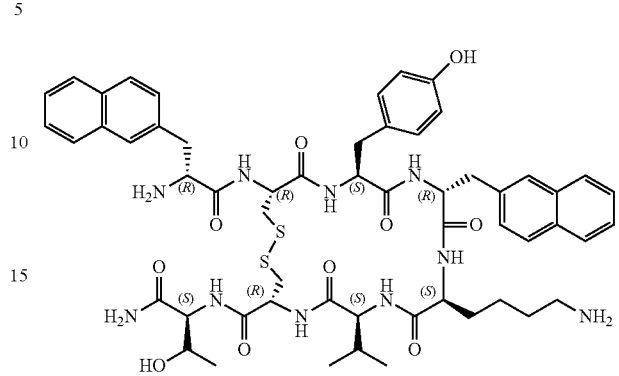

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-β-(2-naphthyl)-D-Ala-OH then Fmoc-L-Tyr(tBu)-OH then Fmoc-L-Cys(Trt)-OH and finally Boc -l3-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-β-(2-naphthyl)-D-Ala⁴-Lys⁵-Val⁶-Cys⁷)-Thr⁸-NH₂.2 CH₃COOH.

HPLC: rt=14.5 min

HRMS (H₂O) m/z: 1129.4651 [M+H]+C, 56; H, 69; N, 10; O, 10; S, 2

Example 8

H-D-2-Nal¹-cyclo(Cys²Tyr³-β-(9-anthryl)- D-Ala⁴-Lys⁵-Val⁶Cys⁷)-Thr⁸-NH₂.2 CH₃COOH

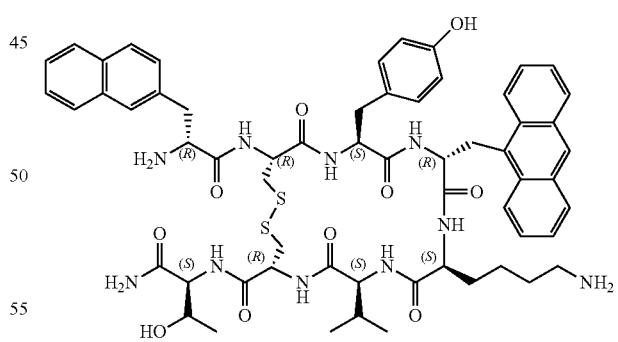

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-β-(9-anthryl)-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-β-(9-anthryl)-D-Ala⁴-Lys⁵-Val⁶Cys⁷)-Thr⁸-NH₂.2 CH₃COOH.

HPLC: rt=10.1 min $^1$H NMR (400 Mhz, D₂O): δ-0.68-0.58 (m, 1H); -0.36-0.24 (m, 1H); 0.68-0.72 (m, 1H); 0.83 (d, J=4.6, 3H); 0.84 (d, J=4.7, 0.92-1.04 (m, 2H); 1.06-1.12 (m, 1H); 1.18 (d, J=6.4, 3H); 2.0 (s, 6H); 2.0-2.08 (m, 1H); 2.4 (dd, J=14.7, J=4.3, 1H); 2.44-2.54 (m, 3H); 2.78 (d, J=7.8, 2H); 2.90 (dd, J=13.2, J=9.6, 1H); 3.01 (dd, J=13.3, J=6.2, 1H); 3.26 (dd, J=10.4, J=4.2, 1H); 3.30-3.36 (m, 1H); 3.38-3.52 (m, 2H); 3.84 (d, J=9.3, 1H); 3.89 (d, J=13.5, 1H); 4.20-4.30 (m, 2H); 4.32 (d, J=3.8, 1H); 4.42 (dd, J=9.1, J=5.8, 1H); 4.66-4.76 (m, 2H); 6.97 (d, J=8.6, 2H); 7.23 (d, J=8.4, 2H); 7.44 (d, J=8.6, 1H); 7.48-7.60 (m, 5H); 7.75 (s, 1H); 7.82-7.94 (m, 5H); 8.05 (d, J=8.0, 2H); 8.4 (s, 1H).

HRMS (H₂O) m/z: 1157.4919 [M+H]+(calc. 1157.4953) C, 60; H, 73; N, 10; O, 10; S, 2

Example 9

H-D-2-Nal¹-cyclo(Cys²-Tyr³-β-(2-fluorenyl)-D-Ala⁴-Lys⁵-Val⁶-Cys⁷)-Thr⁸-NH₂.2 CH₃COOH HPLC: rt=9.8 min $^1$H NMR (400 Mhz, D₂O): δ 0.08-0.20 (m, 1H); 0.32-0.44 (m, 1H); 0.88 (d, J=6.7, 3H); 0.91 (d, J=6.6, 3H); 0.96 (t, J=7.8, 2H); 1.17 (d, J=6.4, 3H); 1.48-1.60 (m, 1H); 1.96 (s, 6H); 1.80-2.08 (m, 2H); 2.10-2.20 (m, 1H); 2.45 (dd, J=14.7, J=3.7, 1H); 2.61 (dd, J=14.8, J=9.7, 1H); 2.68 (dd, J=14.8, J=3.7, 1H); 2.76 (d, J=11.0, 1H); 2.81 (dd, J=11.9, J=9.2, 1H); 2.88-3.00 (m, 3H); 3.35 (dd, J=13.7, J=8.8, 1H); 3.46 (dd, J=13.7, J=5.8, 1H); 3.80 (dd, J=11.0, J=3.2, 1H); 3.88 (s, 2H); 3.92 (d, J=9.8, 1H); 4.19 (dd, J=6.5, J=3.7, 1H); 4.21 (dd, J=11.8, J=5.4, 1H); 4.29 (d, J=3.8, 1H); 4.41 (dd, J=8.8, J=5.8, 1H); 4.63 (t, J=7.5, 1H); 4.86 (dd, J=11.7, J=5.8, 1H); 4.90 (dd, J=11.7, J=5.8, 1H); 6.81 (d, J=8.6, 2H); 7.11 (d, J=8.6, 2H); 7.17 (d, J=8.0, 1H); 7.43 (d, J=1.0, 1H); 7.7 (dd, J=7.4, J=1.1, 1H); 7.40-7.48 (m, 2H); 7.52 (dd, J=9.9, J=3.5, 1H); 7.52 (dd, J=9.9, J=3.1, 1H); 7.62 (d, J=7.3, 1H); 7.78 (s, 1H); 7.79 (d, J=7.8, 1H); 7.82-7.92 (m, 4H).

HRMS (H₂O) m/z: 1167.4774 [M+Na]+(calc. 1167.4772) C, 59; H, 72; Na N, 10; O, 10; S, 2

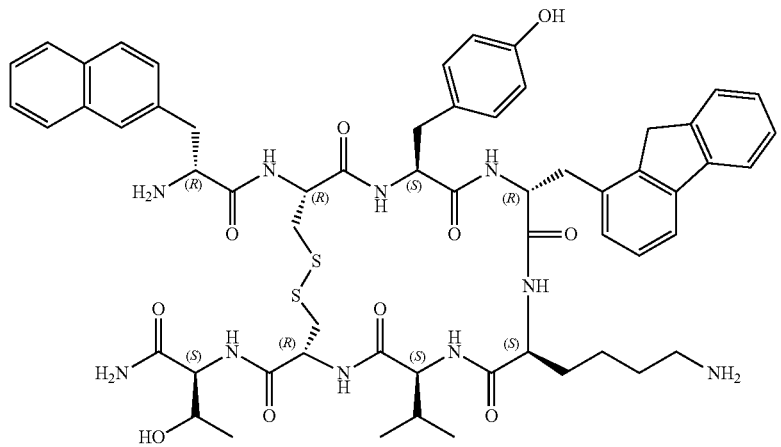

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-f3-(2-fluorenyl)-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²Tyr³-β-(2-fluorenyl)-D-Ala⁴-Lys⁵-Val⁶-Cys⁷)-Thr⁸-NH₂.2 CH₃COOH.

Example 10

H-D-2-Nal¹-cyclo(Cys²-Tyr³-D-Phg⁴-Lys⁵-Val⁶-Cys⁷)-Thr⁸-NH₂.2 CH₃COOH

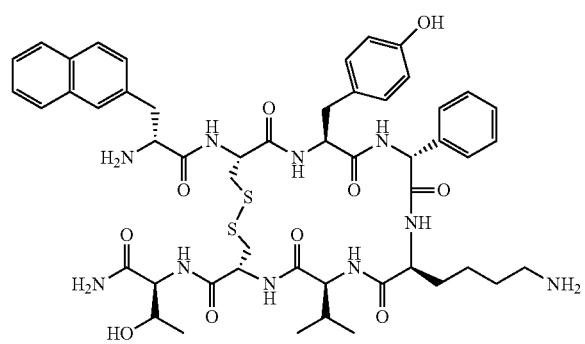 [SMILES: CC(C)[C@@H]1NC(=O)[C@H](CCCCN)NC(=O)[C@@H](c2ccccc2)NC(=O)[C@H](Cc2ccc(O)cc2)NC(=O)[C@@H](NC(=O)[C@H](N)Cc2ccc3ccccc3c2)CSSC[C@@H](C(=O)N[C@H](C(N)=O)C(C)O)NC1=O]

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Phg-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-D-Phg⁴-Lys⁵-Val⁶-Cys⁷)-Thr⁸-NH₂.2 CH₃COOH.

HPLC: rt=8.9 min

¹H NMR (400 Mhz, D₂O): δ 0.93 (d, J=7.0, 3H); 0.96 (d, J=6.8, 3H); 1.10-1.20 (m, 2H); 1.20 (d, J=6.4, 3H); 1.47 (q, J=7.8, 2H); 1.61-1.72 (m, 1H); 1.82-1.92 (m, 1H); 1.97 (s, 6H); 2.12-2.20 (m, 1H); 2.40 (t, J=8.3, 1H); 2.48 (d, J=6.5, 2H); 2.68-2.89 (m, 6H); 2.95 (dd, J=13.3, J=6.0, 1H); 3.31 (dd, J=13.0, J=9.1, 1H); 3.42-3.51 (m, 1H); 4.11 (d, J=8.4, 1H); 4.14 (dd, J=10.0, J=4.2, 1H); 4.39 (dd, J=9.1, J=6.0, 1H); 4.60 (dd, J=9.2, J=6.5, 1H); 4.66 (t, J=6.6, 1H); 4.70-4.78 (m, 2H); 6.69 (d, J=8.1, 2H); 7.03 (d, J=8.4, 2H); 7.15 (d, J=6.4, 2H); 7.32-7.42 (m, 3H); 7.46 (dd, J=8.7, J=0.5, 1H); 7.52-7.60 (m, 2H); 7.78 (bs, 1H); 7.88-7.98 (m, 3H).

HRMS (H₂O) m/z: 1065.4276 [M+Na]+(calc. 1065.4303) C, 51; H, 66; Na N, 10; O, 10; S, 2

Example 11

H-D-2-Nal¹-cyclo(Cys²-Tyr³- D-Homophe⁴-Lys⁵-Val⁶Cys⁷)-Thr⁸-NH₂.2 CH₃COOH

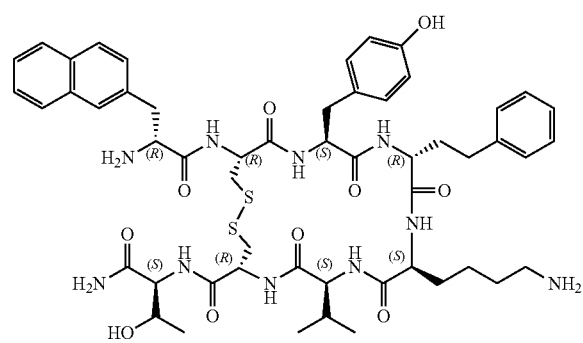

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Homophe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-D-Homophe⁴-Lys⁵-Val⁶Cys⁷)-Thr⁸-NH₂.2 CH₃COOH.

HPLC: rt=8.87 min

¹H NMR (400 Mhz, D₂O): δ 0.89 (d, J=6.7, 3H); 0.92 (d, J=6.7, 3H); 1.17 (d, J=6.4, 3H); 1.26-1.36 (m, 2H); 1.54-1.68 (m, 3H); 1.76-1.84 (m, 2H); 1.86-1.92 (m, 1H); 2.08-2.18 (m, 1H); 1.94 (s, 6H); 2.27 (ddd, J=14.0, J=7.9, J=5.9, 1H); 2.36 (ddd, J=14.2, J=6.4, J=5.6, 1H); 2.48 (dd, J=14.7, J=4.8, 1H); 2.56 (dd, J=14.8, J=8.8, 1H); 2.72 (d, J=3.7, 1H); 2.74 (s, 1H); 2.84-2.82 (m, 3H); 2.96 (dd, J=13.4, J=5.9, 1H); 3.34 (dd, J=13.8, J=8.9, 1H); 3.47 (J=13.7, J=5.8, 1H); 3.88 (dd, J=8.5, J=6.3, 1H); 4.02 (d, J=9.5, 1H); 4.14 (dd, J=9.9, J=4.3, 1H); 4.21 (dd, J=6.5, J=3.9, 1H); 4.30 (d, J=3.9, 1H); 4.40 (dd, J=8.9, J=6.0, 1H); 4.61 (dd, J=9.9, J=6.1, 1H); 4.80-4.88 (m, 2H); 6.82 (d, J=8.6, 2H); 7.03 (dd, J=6.9, J=1.4, 1H); 7.14 (d, J=8.6, 2H); 7.22-7.28 (m, 1H); 7.28-7.34 (m, 2H); 7.45 (dd, J=8.5, J=1.7, 1H); 7.52 (ddd, J=6.9, J=5.1, J=2.0, 1H); 7.53 (ddd, J=6.9, J=5.1, J=2.0, 1H), 7.78 (s, 1H); 7.86-7.93 (m, 3H).

HRMS (H₂O) m/z: 1129.4609 [M+H]+(calc. 1093.4616) C, 53; H, 70; Na N, 10; O, 10; S, 2

Example 12

H-D-2-Nal¹-cyclo(Cys²-Tyr³-p-Br-D-Phe⁴-Lys⁵-Val⁶-Cys⁷)-Thr⁸-NH₂.2 CH₃COOH

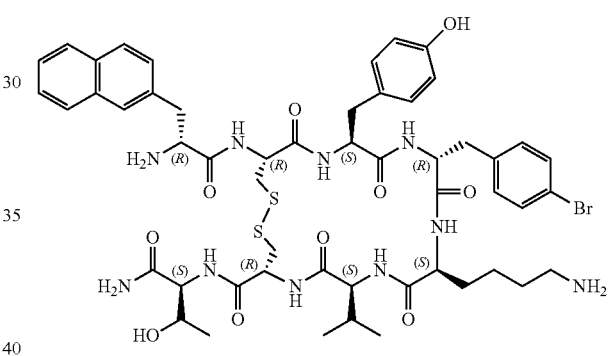

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-p-Br-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-p-Br-D-Phe⁴-Lys⁵-Val⁶-Cys⁷)-Thr⁸-NH₂.2 CH₃COOH.

HPLC: rt=9.5 min

¹H NMR (400 Mhz, D₂O): δ 0.50-0.62 (m, 1H); 0.70-0.82 (m, 1H); 0.91 (d, J=6.8, 3H); 0.99 (d, J=6.6, 3H); 1.18 (d, J=6.6, 3H); 1.30-1.42 (m, 1H); 1.42-1.52 (m, 2H); 1.70-1.80 (m, 1H); 1.96 (s, 6H); 2.12-2.28 (m, 1H); 2.47 (dd, J=14.8, J=3.6, 1H); 2.63 (dd, J=14.6, J=9.8, 1H); 2.68 (dd, J=14.7, J=3.7, 1H); 2.80-2.82 (m, 2H); 2.84-2.96 (m, 4H); 3.36 (dd, J=13.7, J=8.7, 1H); 3.48 (d, J=13.5, J=6.2, 1H); 3.95 (dd, J=11.1, J=3.5, 1H); 3.98 (d, J=10.0, 1H); 4.18-4.24 (m, 2H); 4.30 (d, J=3.8, 1H); 4.42 (dd, J=8.6, J=6.0, 1H); 4.62 (t, J=7.1, 1H); 4.88-4.94 (m, 2H); 6.82 (d, J=8.6, 2H); 7.07 (d, J=8.4,

2H); 7.10 (d, J=8.6, 2H); 7.48-7.52 (m, 3H); 7.53 (dd, J=9.5, J=3.3, 1H); 7.55 (dd, J=9.5, J=3.7, 1H); 7.80 (s, 1H); 7.84-7.94 (m, 3H).

HRMS (H$_2$O) m/z: 1157.3549 and 1159.3585 [M+Na]+ (calc. 1157.3564 and 1159.3544) C, 52; H, 67; Br Na N, 10; O, 10; S, 2

Example 13

H-D-2-Nal$^1$-cyclo(Cys$^2$-Tyr$^3$-p-F-D-Phe$^4$-Lys$^5$-Val$^6$-Cys$^7$)-Thr$^8$-NH$_2$.2 CH$_3$COOH

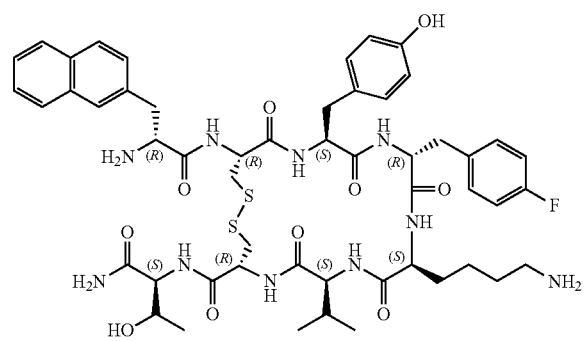

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-p-F-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-p-F-D-Phe$^4$-Lys$^5$-Val$^6$-Cys$^7$)-Thr$^8$-NH$_2$.2 CH$_3$COOH.

HPLC: rt=8.7 min $^1$H NMR (400 Mhz, D$_2$O): δ 0.50-0.62 (m, 1H); 0.72-0.84 (m, 1H); 0.91 (d, J=6.8, 3H); 0.93 (d, J=6.6, 3H); 1.18 (d, J=6.4, 3H); 1.30-1.50 (m, 4H); 1.70-1.80 (m, 1H); 2.02 (s, 6H); 2.14-2.26 (m, 1H); 2.47 (dd, J=15.0, J=3.8, 1H); 2.63 (dd, J=14.8, J=9.9, 1H); 2.68 (dd, J=14.8, J=3.4, 1H); 2.74-2.98 (m, 6H); 3.37 (dd, J=13.8, J=8.8, 1H); 3.48 (dd, J=13.7, J=6.0, 1H); 3.92-4.02 (m, 2H); 4.18-4.24 (m, 2H); 4.30 (d, J=3.8, 1H); 4.43 (dd, J=8.7, J=5.9, 1H); 4.62 (t, J=7.5, 1H); 4.88-4.96 (m, 2H); 6.81 (d, J=8.4, 2H); 7.04-7.18 (m, 6H); 7.47 (dd, J=8.5, J=1.5, 1H); 7.54 (dd, J=9.7, J=3.4, 1H); 7.54 (dd, J=9.6, J=3.4, 1H); 7.80 (s, 1H); 7.84-7.96 (m, 3H).

HRMS (H$_2$O) m/z: 1097.4332 [M+Na]+(calc. 1097.4365) C, 52; H, 67; F N, 10; O, 10; S, 2

Example 14

H-D-2-Nal$^1$-cyclo(Cys$^2$-Tyr$^3$-D-Tyr$^4$-Lys$^5$-Val$^6$-Cys$^7$)-Thr$^8$-NH$_2$.2 CH$_3$COOH

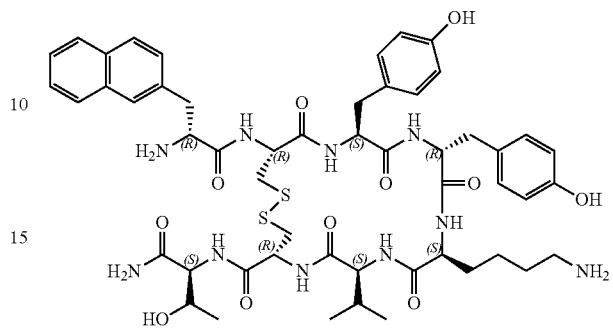

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Tyr-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-D-Tyr$^4$-Lys$^5$-Val$^6$-Cys$^7$)-Thr$^8$-NH$_2$.2 CH$_3$COOH.

HPLC: rt=7.7 min $^1$H NMR (400 Mhz, D$_2$O): δ 0.50-0.64 (m, 1H); 0.66-0.80 (m, 1H); 0.91 (d, J=6.6, 3H); 0.93 (d, J=6.6, 3H); 1.20 (d, J=6.4, 3H); 1.28-1.48 (m, 3H); 1.66-1.78 (m, 1H); 1.89 (s, 6H); 2.12-2.24 (m, 1H); 2.41 (dd, J=14.8, J=3.7, 1H); 2.55 (dd, J=14.8, J=9.5, 1H); 2.64-2.96 (m, 7H); 3.20 (dd, J=13.4, J=9.1, 1H); 3.33 (dd, J=13.2, J=5.7, 1H); 3.92 (dd, J=11.0, J=3.2, 1H); 3.97 (d, J=9.7, 1H); 4.10-4.20 (m, 2H); 4.24 (dq, J=10.5, J=6.4, 1H); 4.32 (d, J=3.8, 1H); 4.60 (t, J=7.3, 1H); 6.80 (t, J=8.3, 4H); 7.02 (d, J=8.2, 2H); 7.09 (d, J=8.4, 2H); 7.43 (d, J=8.4, 1H); 7.48-7.56 (m, 2H); 7.73 (s, 1H); 7.80-7.92 (m, 4H).

HRMS (H$_2$O) m/z: 1073.4578 [M+H]+(calc. 1073.4589) C, 52; H, 69; N, 10; O, 11; S, 2

Example 15

H-D-2-Nal$^1$-cyclo(Cys$^2$-Tyr$^3$-m-F-D-Phe$^4$-Lys$^5$-Val$^6$-Cys$^7$)-Thr$^8$-NH$_2$.2 CH$_3$COOH

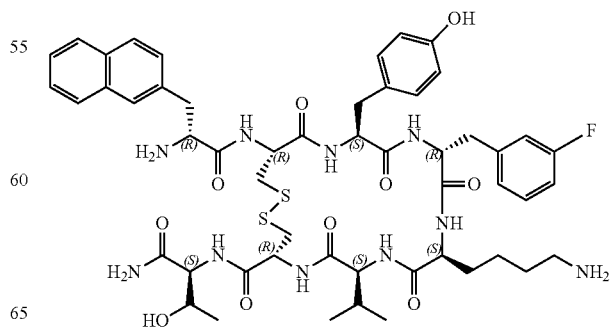

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-m-F-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-m-F-D-Phe$^4$-Lys$^5$-Val$^6$-Cys$^7$)-Thr$^8$-NH$_2$.2 CH$_3$COOH.

HPLC: rt=8.1 min $^1$H NMR (400 Mhz, D$_2$O): δ 0.60-0.72 (m, 1H); 0.74-0.88 (m, 1H); 0.92 (d, J=6.7, 3H); 0.95 (d, J=6.4, 3H); 1.20 (d, J=6.7, 3H); 1.34-1.51 (m, 3H); 1.72-1.82 (m, 1H); 1.90 (s, 1H); 2.15-2.24 (m, 1H); 2.47 (dd, J=14.7, J=3.9, 1H); 2.61 (dd, J=14.8, J=9.8, 1H); 2.70 (dd, J=14.5, J=3.6, 1H); 2.74-2.84 (m, 4H); 2.86-2.94 (m, 3H); 3.32 (dd, J=13.8, J=8.8, 1H); 3.44 (dd, J=13.7, J=5.7, 1H); 4.00 (d, J=9.9, 1H); 4.01 (d, J=10.8, 1H); 4.23 (dd, J=6.4, J=3.8, 1H); 4.25 (dd, J=10.4, J=6.4, 1H); 4.32-4.36 (m, 2H); 4.61 (dd, J=7.1, J=7.9, 1H); 4.88 (dd, J=10.0, J=3.9, 1H); 4.91 (dd, J=11.5, J=3.5, 1H); 6.82 (d, J=8.5, 2H); 6.93 (bd, J=9.7, 1H); 6.98 (d, J=7.7, 1H); 7.01-7.08 (m, 1H); 7.10 (d, J=8.5, 2H); 7.35 (dd, J=14.7, J=7.9, 1H); 7.47 (dd, J=8.6, J=1.3, 1H); 7.52-7.57 (m, 2H); 7.80 (bs, 1H); 7.86-7.89 (m, 1H); 7.90-7.94 (m, 2H).

HRMS (H$_2$O+ACN) m/z: 1075.4492 [M+H]+(calc, 1075.4545) C, 52; H, 68; F N, 10; O, 10; S, 2

Example 16

H-D-2-Nal$^1$-cyclo(Cys$^2$-Tyr$^3$-o-F-D-Phe$^4$-Lys$^5$-Val$^6$-Cys$^7$)-Thr$^8$-NH$_2$.2 CH$_3$COOH

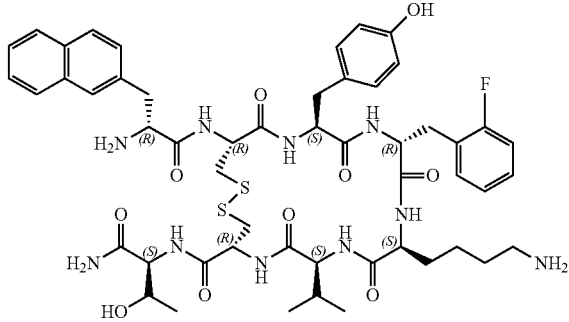

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-o-F-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-o-F-D-Phe$^4$-Lys$^5$-Val$^6$-Cys$^7$)-Thr$^8$-NH$_2$.2 CH$_3$COOH.

HPLC: rt=8.1 min $^1$H NMR (400 Mhz, D$_2$O): δ 0.58-0.70 (m, 1H); 0.74-0.86 (m, 1H); 0.91 (d, J=6.6, 3H); 0.94 (d, J=6.7, 3H); 1.19 (d, J=6.4, 3H); 1.33-1.51 (m, 4H); 1.70-1.80 (m, 1H); 1.97 (s, 6H); 2.12-2.25 (m, 1H); 2.47 (bd, J=13.3, 1H); 2.61 (dd, J=14.6, J=9.3, 1H); 2.64-2.86 (m, 4H); 2.86-2.96 (m, 3H); 3.31-3.41 (m, 1H); 3.42-3.52 (m, 1H); 3.99 (d, J=10.0, 2H); 4.18-4.22 (m, 1H); 4.28 (dd, J=10.3, J=6.1, 1H); 4.31 (d, J=4.3, 1H); 4.42 (bs, 1H); 4.62 (dd, J=7.5, J=7.0, 1H); 4.83-4.93 (m, 2H); 6.82 (d, J=7.9, 2H); 7.06-7.18 (m, 5H); 7.28-7.36 (m, 1H); 7.48 (bd, J=7.3, 1H); 7.56 (bs, 2H); 7.80 (bs, 1H); 7.84-7.98 (m, 3H).

HRMS (H$_2$O) m/z: 1075.4514 [M+H]+(calc, 1075.4545) C, 52; H, 68; N, 10; O, 10; S, 2

Example 17

H-D-2-Nal$^1$-cyclo(Cys$^2$-Tyr$^3$-3,5-diF-D-Phe$^4$-Lys$^5$-Val$^6$-Cys$^7$)-Thr$^8$-NH$_2$.2 CH$_3$COOH

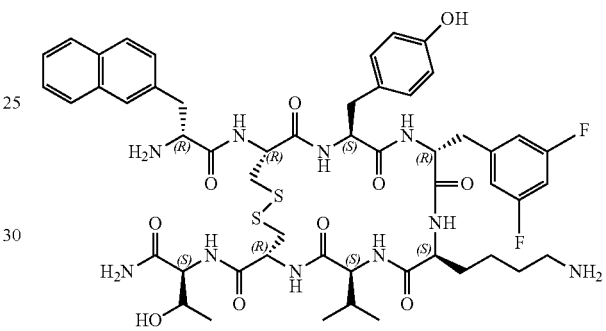

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-3,5-diF-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-3,5-diF-D-Phe$^4$-Lys$^5$-Val$^6$-Cys$^7$)-Thr$^8$-NH$_2$.2 CH$_3$COOH.

HPLC: rt=8.8 min $^1$H NMR (400 Mhz, D$_2$O): δ 0.75-0.85 (m, 1H); 0.92 (d, J=6.6, 3H); 0.96 (d, J=6.6, 3H); 1.20 (d, J=6.6, 3H); 1.40-1.55 (m, 3H); 1.77-1.87 (m, 1H); 1.90 (s, 6H); 2.20 (dd, J=13.2, J=6.6, 1H); 2.49 (dd, J=14.8, J=4.0, 1H); 2.62 (dd, J=14.7, J=9.8, 1H); 2.70 (dd, J=14.7, J=3.8, 1H); 2.79 (dd, J=14.7, J=11.4, 1H); 2.81-2.95 (m, 6H); 3.34 (dd, J=13.6, J=9.0, 1H); 3.45 (dd, J=13.6, J=5.8, 1H); 4.01 (d, J=9.9, 1H); 4.06 (dd, J=10.8, J=3.6, 1H); 4.20-4.28 (m, 2H); 4.33 (d, J=3.8, 1H); 4.35 (dd, J=8.8, J=6.0, 1H); 4.61 (d, J=7.7, 1H); 4.89 (dd, J=9.8, J=4.1, 1H); 4.92 (dd, J=11.3, J=3.6, 1H); 6.75-6.84 (m, 4H); 6.86-6.92 (m, 1H); 7.09 (d, J=8.6, 2H); 7.48 (dd, J=8.2, J=1.1, 1H); 7.52-7.59 (m, 2H); 7.80 (s, 1H); 7.85-7.95 (m, 3H).

HRMS (H$_2$O) m/z: 1093.4406 [M+H]+(calc. 1093.4451) C, 52; H, 67; N, 10; O, 10; F, 2; S, 2

Example 18

H-D-2-Nal¹-cyclo(Cys²-Tyr³-m-Br-D-Phe⁴-Lys⁵-Val⁶-Cys⁷)-Thr⁸-NH₂.2 CH₃COOH

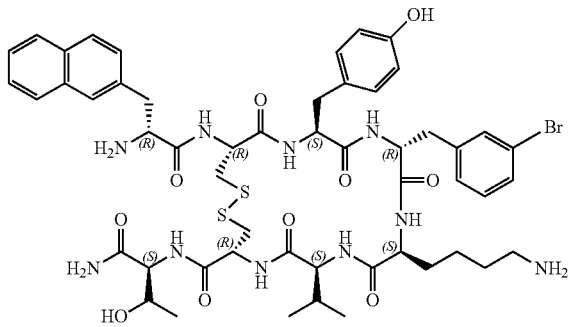

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-m-Br-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-m-Br-D-Phe⁴-Lys⁵-Val⁶-Cys⁷)-Thr⁸-NH₂.2 CH₃COOH.

HPLC: rt=9.0 min

¹H NMR (400 Mhz, D₂O): δ 0.52-0.68 (m, 1H); 0.76-0.90 (m, 1H); 0.92 (d, J=6.8, 3H); 0.95 (d, J=6.6, 3H); 1.21 (d, J=6.4, 3H); 1.30-1.54 (m, 3H); 1.70-1.82 (m, 1H); 1.93 (s, 6H); 2.12-2.27 (m, 1H); 2.48 (dd, J=14.8, J=3.7, 1H); 2.63 (dd, J=14.8, J=9.7, 1H); 2.70 (dd, J=14.5, J=3.5, 1H); 2.74-2.99 (m, 7H); 2.28 (dd, J=14.0, J=9.1, 1H); 3.49 (dd, J=13.7, J=5.7, 1H); 3.95-4.05 (m, 2H); 4.19-4.27 (m, 2H); 4.32 (d, J=3.8, 1H); 4.43 (dd, J=8.7, J=5.7, 1H); 4.63 (dd, J=7.7, J=7.2, 1H); 4.87-4.95 (m, 1H); 6.83 (d, J=8.1, 2H); 7.11 (d, J=8.4, 2H); 7.16 (d, J=7.5, 1H); 7.27 (t, J=7.8, 1H); 7.36 (s, 1H); 7.48 (s, 1H); 7.50 (s, 1H); 7.53-7.60 (m, 2H); 7.81 (s, 1H); 7.86-7.96 (m, 3H).

HRMS (H₂O) m/z: 1135.3741 and 1137.3704 [M+H]+ (calc. 1135.3745 and 1137.3724) C, 52; H, 68; Br N, 10; O, 10; S, 2

Example 19: H-D-2-Nal¹-cyclo(Cys²-Tyr³-o-Br-D-Phe⁴-Lys⁵-Val⁶-Cys⁷)-Thr⁸-NH₂.2 CH₃COOH

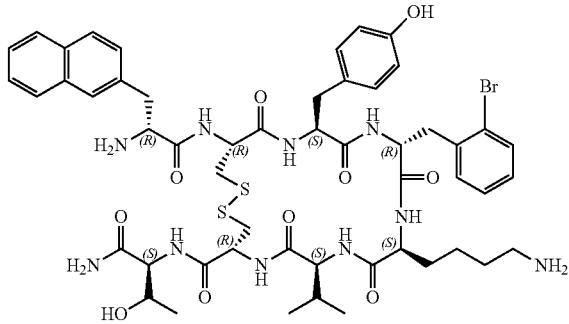

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-o-Br-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-o-Br-D-Phe⁴-Lys⁵-Val⁶-Cys⁷)-Thr⁸-NH₂.2 CH₃COOH.

HPLC: rt=9.3 min

¹H NMR (400 Mhz, D₂O): δ 0.52-0.68 (m, 1H); 0.76-0.90 (m, 1H); 0.92 (d, J=6.8, 3H); 0.95 (d, J=6.6, 3H); 1.21 (d, J=6.4, 3H); 1.30-1.54 (m, 3H); 1.70-1.82 (m, 1H); 1.93 (s, 6H); 2.12-2.27 (m, 1H); 2.48 (dd, J=14.8, J=3.7, 1H); 2.63 (dd, J=14.8, J=9.7, 1H); 2.70 (dd, J=14.5, J=3.5, 1H); 2.74-2.99 (m, 7H); 2.28 (dd, J=14.0, J=9.1, 1H); 3.49 (dd, J=13.7, J=5.7, 1H); 3.95-4.05 (m, 2H); 4.19-4.27 (m, 2H); 4.32 (d, J=3.8, 1H); 4.43 (dd, J=8.7, J=5.7, 1H); 4.63 (dd, J=7.7, J=7.2, 1H); 4.87-4.95 (m, 1H); 6.83 (d, J=8.1, 2H); 7.11 (d, J=8.4, 2H); 7.16 (d, J=7.5, 1H); 7.27 (t, J=7.8, 1H); 7.36 (s, 1H); 7.48 (s, 1H); 7.50 (s, 1H); 7.53-7.60 (m, 2H); 7.81 (s, 1H); 7.86-7.96 (m, 3H).

HRMS (H₂O) m/z: 1135.3749 and 1137.3723 [M+H]+ (calc. 1135.3745 and 1137.3724) C, 52; H, 68; Br N, 10; O, 10; S, 2

Example 20

H-D-2-Nal¹-cyclo(Cys²-Tyr³-p-nitro-D-Phe⁴-Lys⁵-Val⁶-Cys⁷)-Thr⁸-NH₂.2 CH₃COOH

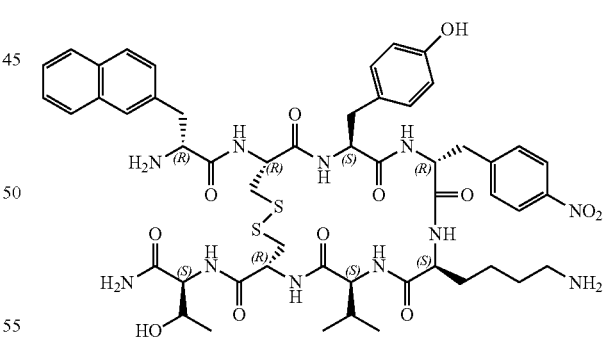

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-p-nitro-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-p-nitro-D-Phe$^4$-Lys$^5$-Val$^6$-Cys$^7$)-Thr$^8$-NH$_2$.2 CH$_3$COOH.

HPLC: rt=9.6 min $^1$H NMR (400 Mhz, D$_2$O): δ 0.64-0.76 (m, 1H); 0.78-0.90 (m, 1H); 0.91 (d, J=6.7, 3H); 0.94 (d, J=6.6, 3H); 1.19 (d, J=6.5, 3H); 1.35-1.47 (m, 3H); 1.72-1.82 (m, 1H); 1.89 (s, 6H); 2.11-2.21 (m, 1H); 2.47 (dd, J=14.6, J=4.0, 1H); 2.59 (dd, J=14.7, J=9.8, 1H); 2.69 (dd, J=14.7, J=3.9, 1H); 2.72-2.81 (m, 3H); 2.84 (d, J=8.0, 2H); 2.94 (d, J=2.9, 1H); 3.00 (s, 1H); 3.30 (dd, J=13.6, J=9.0, 1H); 3.42 (dd, J=13.7, J=5.7, 1H); 3.99 (m, 2H); 4.21 (dd, J=6.6, J=4.0, 1H); 4.26-4.34 (m, 3H); 4.59 (t, J=7.6, 1H); 4.82-4.92 (m, 3H); 6.75 (d, J=8.5, 2H); 7.05 (d, J=8.5, 2H); 7.35 (d, J=8.7, 2H); 7.46 (dd, J=8.6, J=1.2, 1H); 7.50-7.56 (m, 2H); 7.78 (bs, 1H); 7.84-7.88 (m, 1H); 7.88-7.94 (m, 2H).

HRMS (H$_2$O) m/z: 1102.4476 [M+H]+(calc. 1102.4490) C, 52; H, 68; N, 11; O, 12; S, 2

Example 21

H-D-2-Nal$^1$-cyclo(Cys$^2$-Tyr$^3$-p-Ph-D-Phe$^4$-Lys$^5$-Val$^6$-Cys$^7$)-Thr$^8$-NH$_2$.2 CH$_3$COOH

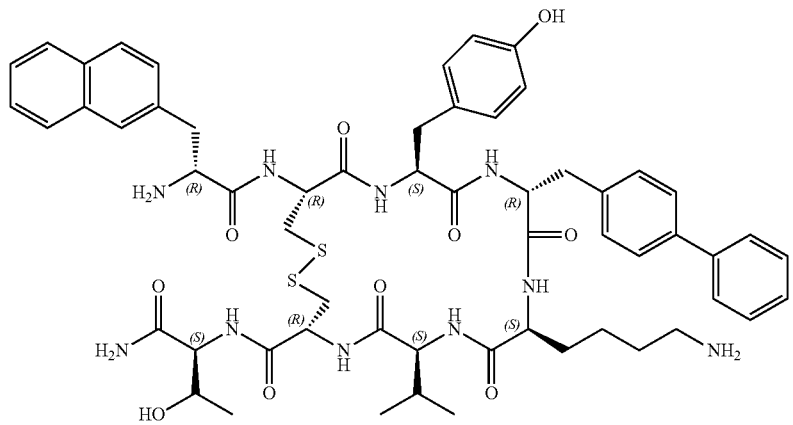

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-p-Ph-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-p-Ph-D-Phe$^4$-Lys$^5$-Val$^6$-Cys$^7$)-Thr$^8$-NH$_2$.2 CH$_3$COOH.

HPLC: rt=9.9 min $^1$H NMR (400 Mhz, D$_2$O): δ 0.51-0.62 (m, 1H); 0.62-0.72 (m, 1H); 0.90 (d, J=6.6, 3H); 0.93 (d, J=6.6, 3H); 1.20 (d, J=6.3, 3H); 1.23-1.28 (m, 1H); 1.28-1.36 (m, 1H); 1.62-1.73 (m, 1H); 1.89 (s, 6H); 2.12-2.24 (m, 1H); 2.35-2.46 (m, 3H); 2.54 (dd, J=14.6, J=9.5, 1H); 2.67-2.82 (m, 2H); 2.82-2.98 (m, 4H); 3.20 (dd, J=13.3, J=9.2, 1H); 3.36 (dd, J=13.4, J=5.6, 1H); 3.91 (dd, J=10.9, J=3.4, 1H); 3.96 (d, J=9.8, 1H); 4.15 (dd, J=8.2, J=6.2, 1H); 4.20-4.30 (m, 2H); 4.32 (d, J=3.9, 1H); 4.31 (dd, J=7.7, J=7.2, 1H); 4.84-4.90 (m, 2H); 6.81 (d, J=6.8, 2H); 7.09 (d, J=8.4, 2H); 7.25 (d, J=7.9, 2H); 7.41-7.46 (m, 2H); 7.48-7.58 (m, 4H); 7.66 (d, J=8.0, 2H); 7.71 (d, J=7.4, 2H); 7.75 (bs, 1H); 7.83-7.87 (m, 1H); 7.87-7.92 (m, 2H).

HRMS (H$_2$O) m/z: 1133.5002 [M+H]+(calc. 1133.4953) C, 58; H, 73; N, 10; O, 10; S, 2

Example 22

H-D-2-Nal$^1$-cyclo(Cys$^2$-Tyr$^3$-p-2-(2-methoxyethoxy)ethoxy)-D-Phe$^4$-Lys$^5$-Val$^6$-Cys$^7$)-Thr$^8$-NH$_2$].2 CH$_3$COOH

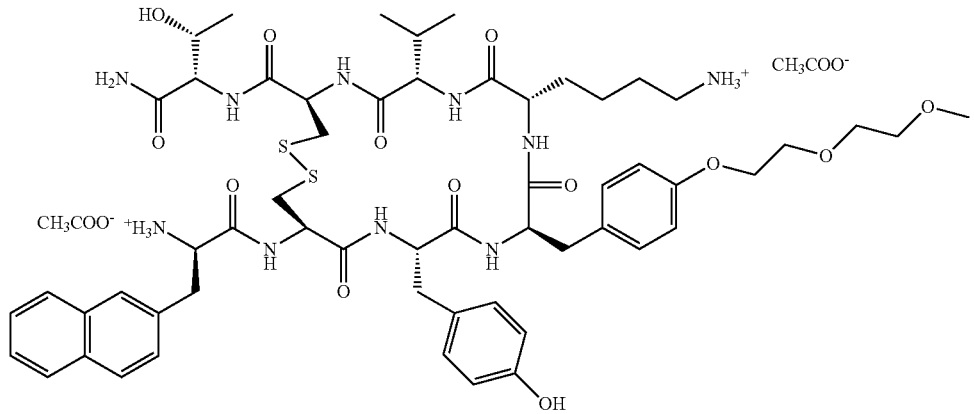

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-p-2-(2-methoxyethoxy)ethoxy)-D-Phe-OH then Fmoc-L-Tyr(tBu)-OH then Boc-L-Cys(Trt)-OH and finally Fmoc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-p-2-(2-methoxyethoxy)ethoxy)-D-Phe$^4$-Lys$^5$-Val$^6$-Cys$^7$)-Thr$^8$-NH$_2$].2 CH$_3$COOH.

$^1$H NMR (400 MHz, D$_2$O): δ 0.64-0.76 (m, 1H); 0.76-0.88 (m, 1H); 0.93 (d, J=6.9, 3H); 0.96 (d, J=6.9, 3H); 1.23 (d, J=6.3, 3H); 1.35-1.52 (m, 2H); 1.72-1.82 (m, 1H); 1.91 (s, 6H); 2.13-2.24 (m, 1H); 2.43 (dd, J=14.6, J=4.8, 1H); 2.54 (dd, J=14.5, J=9.3, 1H); 2.70-2.95 (m, 4H); 3.19 (dd, J=13.1, J=9.6, 1H); 3.36 (s, 3H); 3.60 (t, J=3.4, 1H); 3.61 (t, J=4.4, 1H); 3.71 (t, J=4.4, 1H); 3.72 (t, J=3.4, 1H); 3.84-3.89 (m, 2H); 3.99 (d, J=10.8, 1H); 4.00 (d, J=4.01, 1H); 4.07-4.14 (m, 1H); 4.16-4.20 (m, 2H); 4.23-4.30 (m, 2H); 4.35 (d, J=3.9, 1H); 4.60 (dd, J=7.6, J=6.8, 1H); 4.83-4.88 (m, 2H); 6.82 (d, J=8.4, 2H); 6.96 (d, J=8.6, 2H); 7.07 (d, J=8.4, 2H); 7.13 (d, J=8.6, 2H); 7.46 (dd, J=8.5, J=1.3, 1H); 7.51-7.56 (m, 2H); 7.76 (bs, 1H); 7.85-7.94 (m, 3H).

Example 23

H-2-Nal$^1$-cyclo(D-Cys$^2$-D-Tyr$^3$-Trp$^4$-D-Lys$^5$-D-Val$^6$-D-Cys$^7$)-D-Thr$^8$-NH$_2$.2 CH$_3$COOH

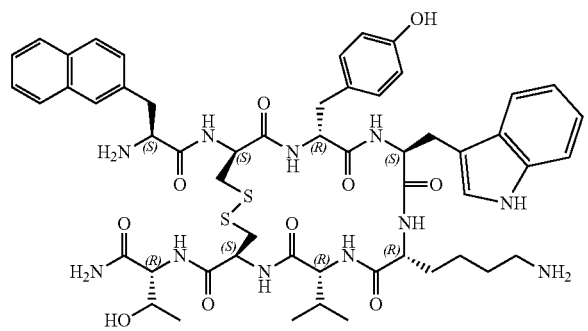

The open peptide is obtained according to the protocol described previously by successive deprotection of the Fmoc (9-fluorenylmethyloxycarbonyl) group and coupling of the following amino acid on a solid support in the following order: Fmoc-D-Thr(tBu)-OH then Fmoc-D-Cys(Trt)-OH then Fmoc-D-Val-OH then Fmoc-D-Lys(Boc)-OH then Fmoc-L-Trp-OH then Fmoc-D-Tyr(tBu)-OH then Fmoc-D-Cys(Trt)-OH and finally Boc-β-(2-naphthyl)-L-Ala-OH.

The compound is cyclized by the formation of a disulphide bridge followed by cleavage of the resin, purified, and finally obtained in the form of acetate according to the operating method described previously in order to produce the compound H-2-Nal$^1$-cyclo(D-Cys$^2$-D-Tyr$^3$-Trp$^4$-D-Lys$^5$-D-Val$^6$-D-Cys$^7$)-D-Thr$^8$-NH$_2$.2 CH$_3$COOH.

HPLC: rt=9.87 min $^1$H NMR (400 MHz, D$_2$O): δ 0.10-0.22 (m, 1H), 0.32-0.46 (m, 1H), 0.90 (d, J=7.6, 3H), 0.91 (d, J=7.3, 3H), 1.10-1.30 (m, 4H) 1.19 (d, J=6.2, 3H), 1.50-1.62 (m, 1H), 1.95 (s, 6H), 2.10-2.20 (m, 1H), 2.45 (dd, J=14.5, J=3.9, 1H), 2.52-2.64 (m, 3H), 2.70 (dd, J=14.8, J=3.8, 1H), 2.78 (dd, J=14.3, J=11.7, 1H), 2.90-3.60 (m, 4H), 3.35 (dd, J=13.5, J=9.0, 1H), 3.46 (dd, J=14.0, J=6.0, 1H), 3.81 (dd, J=10.9, J=3.4, 1H), 3.95 (d, J=9.4, 1H), 4.18-4.27 (m, 2H), 4.31 (d, J=3.6, 1H), 4.42 (dd, J=8.5, J=5.9, 1H), 4.64 (t, J=7.4, 1H), 4.83-4.92 (m, 2H), 6.84 (d, J=8.6, 2H), 7.12 (d, J=8.6, 2H), 7.16 (t, J=7.1, 1H), 7.22 (t, J=7.1, 1H), 7.43-7.49 (m, 2H), 7.50-7.57 (m, 3H), 7.77 (bs, 1H), 7.83-7.88 (m, 1H), 7.90 (bd, J=8.9, 2H).

HRMS (H$_2$O) m/z: 1096.4749 [M+H]+

Example 24

H-D-2-Nal$^1$-cyclo(Cys$^2$-Tyr$^3$-cyclohexyl-D-Ala$^4$-Lys$^5$-Val$^6$-Cys$^7$)-Thr$^8$-NH$_2$.2 CH$_3$COOH

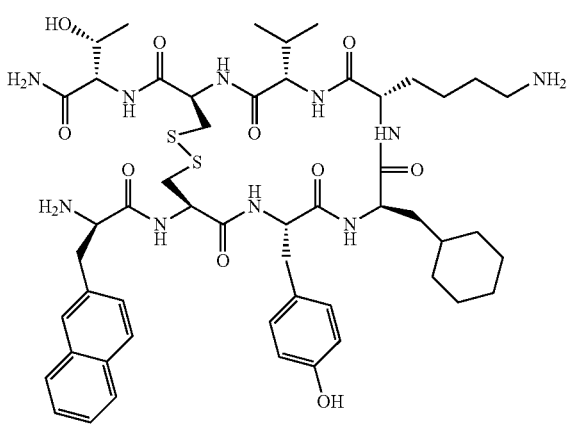 [SMILES: CC(C)[C@@H]1NC(=O)[C@H](CCCCN)NC(=O)[C@@H](CC2CCCCC2)NC(=O)[C@H](Cc2ccc(O)cc2)NC(=O)[C@@H](NC(=O)[C@H](N)Cc2ccc3ccccc3c2)CSSC[C@@H](C(=O)N[C@H](C(N)=O)[C@@H](C)O)NC1=O]

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-cyclohexyl-D-Ala-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal$^1$-cyclo(Cys$^2$-Tyr$^3$-cyclohexyl-D-Ala$^4$-Lys$^5$-Val$^6$-Cys$^7$)-Thr$^8$-NH$_2$.2 CH$_3$COOH.

HPLC: rt=5.13 min $^1$H NMR (400 Mhz, D$_2$O): δ 0.6-0.8 (m, 1H), 0.8 (d, J=7.5, 3H), 0.84 (d, J=7.3, 3H), 0.95 (bs), 1.1 (d, J=7.3, 3H), 1.14-1.35 (m, 4H), 1.35-1.65 (m, 6H), 1.7-1.94 (m, 5H), 1.98-2.1 (m, 1H), 2.32-2.5 (m, 2H), 2.6 (d, J=7.4, 1H), 2.72-2.92 (m, 4H), 3.18 (dd, J=9.2, J=13.4, 1H), 3.3 (dd, J=8, J=13.4, 1H), 3.85 (t, J=7.4, 1H), 3.9 (d, J=9.5, 1H), 4-4.1 (m, 2H), 4.18 (m, 2H), 4.4 (dd, J=6.2, J=9.5, 1H), 6.65 (d, J=8.3, 2H), 6.97 (d, J=8.4, 2H), 7.35 (d, J=8.3, 1H), 7.37-7.42 (m, 2H), 7.62 (s, 1H), 7.7-7.8 (m, 2H), 8.28 (s, 1H).

HRMS (H$_2$O) m/z: 1063.51245 [M+H]+(calc. 1063.510909) C, 52; H, 75; N, 10; O, 10; S, 2

Example 25

H-D-2-Nal¹-cyclo(Cys²-Tyr³-p-phenylazo-D-Phe⁴-Lys⁵-Val⁶-Cys⁷)-Thr⁸-NH₂.2 CH₃COOH

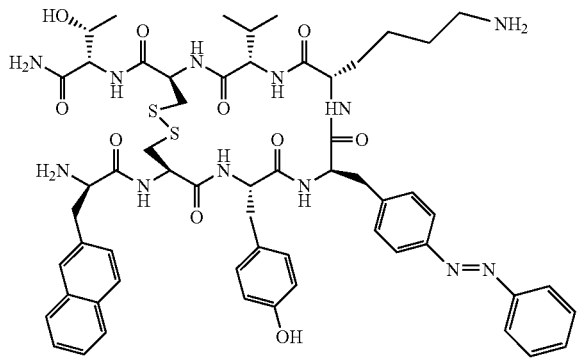 [SMILES: CC(C)[C@@H]1NC(=O)[C@H](CCCCN)NC(=O)[C@@H](Cc2ccc(/N=N/c3ccccc3)cc2)NC(=O)[C@H](Cc2ccc(O)cc2)NC(=O)[C@@H](NC(=O)[C@H](N)Cc2ccc3ccccc3c2)CSSC[C@@H](C(=O)N[C@H](C(N)=O)[C@@H](C)O)NC1=O]

The open peptide is obtained according to the protocol described previously by successive deprotection of the Fmoc (9-fluorenylmethyloxycarbonyl) group and coupling of the following amino acid on a solid support in the following order: Fmoc-L-Thr(tBu)-OH then Fmoc-L-Cys(Trt)-OH then Fmoc-L-Val-OH then Fmoc-L-Lys(Boc)-OH then Fmoc-4-phenylazo-D-Phe-OH then Fmoc-L-Tyr(tBu)-OH then Fmoc-L-Cys(Trt)-OH and finally Boc-β-(2-naphthyl)-D-Ala-OH.

The compound is cyclized by the formation of a disulphide bridge followed by cleavage of the resin, purified, and finally obtained in the form of acetate according to the operating method described previously in order to produce the compound H-D-2-Nal¹-cyclo(Cys²-Tyr³-4-phenylazo-D-Phe⁴-Lys⁵-Val⁶-Cys⁷)-Thr⁸-NH₂.2 CH₃COOH.

HPLC: rt=6.0 min $^1$H NMR (400 Mhz, D₂O): δ 0.6-0.85 (m, 1H), 0.9 (d, J=7.4, 3H), 0.93 (d, J=7.3, 3H), 1.2 (d, J=7.4, 3H), 1.27-1.56 (m, 2H), 1.68-2.07 (m, 10H), 2.1-2.5 (m, 1H), 2.55-3.07 (m, 8H), 3.35 (dd, J=8.9, J=13, 1H), 3.47 (dd, J=5.6, J=13, 1H), 3.99 (d, J=9.9, 1H), 4.21-4.25 (m, 1H), 4.32 (d, J=3.8, 2H), 4.33-4.4 (m, 1H), 4.57-4.98 (m, 4H), 6.81 (d, J=8.4, 2H), 6.91 (m, 1H), 7.1 (t, J=8.8, 2H), 7.21-7.35 (m, 1H), 7.37 (d, J=8.3, 2H), 7.48 (d, J=8.4, 1H), 7.55 (m, 2H), 7.63 (m, 2H), 7.78-7.94 (m, 8 H).

HRMS (H₂O) m/z: 1161.50281 [M+H]+(calc. 1161.501407) C, 58; H, 73; N, 12; O, 10; S, 2

2. Study of the Compounds According to the Invention

2.1 Activity of the Octapeptide Compounds on the Somatostatin Receptors

2.1.1 Protocol for Measurement of the Affinity of the Peptides for the Somatostatin Receptors The affinity of the compounds of the invention for the somatostatin receptors is determined by measurement of the inhibition of the bond of [125I-Tyr11]SRIF-14 to membrane preparations of transfected CHO-K1 cells.

The CHO-K1 cells expressing in a stable fashion each of the sub-types of somatostatin receptors are collected with 0.5 mM of EDTA and centrifuged at 500 g for 5 minutes at 4° C. The pellet is re-suspended in phosphate buffer (PBS) and centrifuged at 500 g for 5 minutes at 4° C. The pellet is re-suspended in Tris 50 mM buffer at pH 7.4 and centrifuged at 500 g for 5 minutes at 4° C. The cells are lyzed by sonication and centrifuged at 39,000 g for 10 minutes. The pellet is re-suspended in Tris 50 mM buffer at pH 7.4, an aliquot is removed for assaying the proteins and the remainder is centrifuged at 50,000 g for 10 minutes. The membranes obtained in this last pellet are stored at −80° C.

Measurement of the competitive inhibition of the bond of [125I-Tyr11]SRIF-14 (Perkin Elmer) on each of the sub-types of somatostatin receptors is carried out in duplicate in 96-well polypropylene plates. The cell membranes (5 to 20 pg of proteins/well) are incubated with [125I-Tyr11]SRIF-14 (0.05 to 0.1 nM) for 50 to 90 minutes at 37° C. (conditions dependent on the sub-type of receptor) in a HEPES buffer medium 50 mM pH 7.4, comprising 0.2% bovine serum albumin (BSA), MgCl2 5 mM, Trasylol 200 KIU/mL, Bacitracin 0.02 mg/mL, phenylmethylsulphonyl fluoride 0.02 mg/mL.

The bound [125I-Tyr11]SRIF-14 is separated from the free [125I-Tyr11]SRIF-14 by filtration through GF/C glass fibre plates (Unifilter, Perkin Elmer) pre-impregnated with 0.1% polyethylenimine (P.E.I.), using a Filtermate 96 (Perkin Elmer). The filters are washed with Tris-HCl buffer 50 mM, pH 7.4 at 4° C. and the radioactivity present is determined using a counter (TopCount, Perkin Elmer).

The data are analyzed by computer-assisted non-linear regression using XLfit 4.2 (IDBS) software.

2.1.2 Results

Examples 1, 2, 3, 4, 5, 6, 8, 9, 10, 11, 12, 13, 14, 15, 16, 17, 18, 19, 20, 21, 24 and 25 have an affinity for the somatostatin receptors sub-type 2 less than or equal to 5 µM.

Examples 1, 2, 3, 5, 6, 8, 9, 10, 11, 12, 13, 14, 15, 16, 17, 18, 19, 20, 21, 24 and 25 have an affinity for the somatostatin receptors sub-type 2 less than or equal to 700 nM.

Examples 1, 2, 6, 8, 9, 11, 12, 13, 14, 15, 16, 17, 18, 19, 20, 21, 24 and 25 have an affinity for the somatostatin receptors sub-type 2 less than or equal to 50 nM.

Examples 1, 6, 12, 13, 14, 15, 16, 17, 18, 19, 20 and 24 have an affinity for the somatostatin receptors sub-type 2 less than or equal to 5 nM.

Examples 1, 2, 3, 5, 6, 8, 9, 10, 11, 12, 13, 14, 15, 16, 17, 18, 19, 20, 21, 24 and 25 have an affinity for the somatostatin receptors sub-type 5 less than or equal to 5 µM.

Examples 1, 2, 6, 8, 9, 11, 12, 13, 14, 15, 16, 17, 18, 19, 20, 21, 24 and 25 have an affinity for the somatostatin receptors sub-type 5 less than or equal to 1 µM.

Examples 1, 6, 8, 9, 12, 15, 17, 18, 19, 21 and 24 have an affinity for the somatostatin receptors sub-type 5 less than or equal to 100 nM.

2.2 Physico-chemical Properties of the Octapeptide Compounds

The peptides obtained are the subject of a study of their self-assembly properties.

The procedure used comprises three stages: putting the peptides in solution and macroscopic analysis; spectroscopic and microscopic analyses of the structures formed and by small-angle X-ray scattering (SAXS) analyses.

2.2.1 Putting the Peptides in Solution and Macroscopic Analysis

The first stage of the characterization of the derivatives is the production of a range of concentrations from 3 to 15% by mass of peptide in water. Gelling of the solution indicates the presence of self-assembled structures which can be nanotubes but can also be fibres or other self-organised structures.

2.2.2 Spectroscopic and Microscopic Analyses of the Structures Formed

The object of this stage is to verify the presence of self-assembled structures, to characterize their self-assembly and to visualize them by microscopy.

Infrared spectroscopy makes it possible to obtain information on the method of stacking the peptides in the self-assemblies. The amide band spectrum, reflecting the absorption spectra of the carbonyl functions of the peptide backbone, gives information on the type of hydrogen bond in which these groups are involved (H bonds leading to the formation of the β sheet, a helix or also a loop or random conformation) and consequently on the secondary and tertiary structure of the peptides in solution and self-assembled. The attenuated total reflection technique (ATR-FTIR) uses a crystal on which the solid or liquid sample is deposited. The infrared light is guided through this crystal at an angle which allows it to be reflected several times inside the crystal, which increases the sensitivity of the technique. Due to the performance of this device, it is then possible perform measurements on relatively dilute solutions. The beam penetrates a few microns into the sample deposited on the crystal, which means that only the molecules/structures which are deposited on the surface of the crystal are analyzed. Moreover, this technique is non-destructive.

The assembled structures are then visualized by transmission electron microscopy (TEM). This very powerful technique, allowing magnifications greater than 500,000 times, is one of the few techniques capable of visualizing structures on the nanometric scale. The sample is subjected to an electron beam. The visualization of the transmitted beam is produced either by a photoluminescent screen, or by a CCD camera. The sample in the microscope being under vacuum, it is samples dried after staining with uranyl salts in order to increase contrast which are observed.

The peptide in solution is firstly deposited on a copper grid covered with a film of carbon. After deposition of the materiel, the excess liquid is eliminated. In the same way, the solution of colorant, in our case uranyl acetate, is deposited on the grid, the excess is eliminated and the grid is dried in the open air. It can then be introduced into the microscope.

2.2.3 Analyses by Small Angle X-ray Scattering (SAXS)

The samples, liquids or gels, are introduced into a capillary column and subjected to a monochromatic flow of X-rays. The intensity diffused is measured as a function of the scattering angle with respect to the incident angle.

The diffusion patterns thus obtained must be the subject of a correlation with a close theoretical model of the structures present in the sample. In the case where the peptides have self-assembled in the form of hollow nanotubes, the modelling of the experimental data with the theoretical diffusion produced by infinitely long hollow columns makes it possible to determine with precision the diameter of the columns and to estimate their wall thickness (Valery et al. in *Biophysical journal*, 2004, 86(4), 2484-2501 and *Proc. Natl. Acad. Sci.*, 2003, 100(18) 10258-10262). For polydisperse, nanotubular, fibrilar, micellar or lamellar self-assemblies, it is the correlation of the spectroscopic, microscopic and XR scattering data which makes it possible to estimate a size range for the objects observed.

2.2.4 Results

The results of the analysis of the physico-chemical properties of the compounds are presented in Table 1 below:

TABLE 1

| Example | Assembly |
|---|---|
| 1 | 20 nm monodisperse nanotube |
| 2 | 12 nm monodisperse nanotube |
| 3 | 9.3 nm monodisperse nanotube |
| 4 | fibres |
| 5 | soluble |
| 6 | 35 nm monodisperse nanotube |
| 7 | insoluble |
| 8 | insoluble |
| 9 | 22 nm monodisperse nanotube |
| 10 | fibres |
| 11 | soluble |
| 12 | 17 nm monodisperse nanotube |
| 13 | 17 nm monodisperse nanotube |
| 14 | 18 nm monodisperse nanotube |
| 15 | 15.6 nm monodisperse nanotube |
| 16 | 17 nm monodisperse nanotube |
| 17 | 15.3 nm monodisperse nanotube |
| 18 | 18.4-18.8 nm monodisperse nanotube |
| 19 | approximately 29 nm polydisperse nanotube |
| 20 | 17.6 nm monodisperse nanotube |
| 21 | insoluble |
| 22 | 17.4 nm monodisperse nanotube |
| 23 | 24.4 nm monodisperse nanotube |
| 24 | fibres |
| 25 | 10 nm monodisperse nanotube |

Certain peptides make it possible to obtain monodisperse nanotubes, whilst others assemble into fibres or into polydisperse nanotubes. Finally, a few are soluble, or on the other hand insoluble under the operating conditions mentioned above.

The derivatives which self-assemble into monodisperse peptide nanotubes are the following: Examples 1, 2, 3, 6, 9, 12, 13, 14, 15, 16, 17, 18, and 20. A range of diameters from 9.3 to 35 nm is obtained.

The derivative of Example 19 assembles into nanotubes with polydisperse diameters.

The derivatives making it possible to obtain self-assembled fibres are the following: Examples 4 and 10.

The derivatives which are soluble at the concentrations studied are the following: Examples 5 and 11.

Finally, the derivatives which are insoluble at the concentrations studied are the following: Examples 7, 8 and 21.

A study of the compounds in other concentration ranges could reveal a change in these behaviours.

2.3 Rheology of the Octapeptide Compounds

The viscous and viscoelastic properties of the solutions/gels of the compounds according to the invention can be studied by rheology according to the operating methods described hereafter.

2.3.1 Equipment and Measurement Conditions

The measurements are in general carried out using a rheometer of "Control Stress Haake 600" type (Haake, Germany) equipped with a cone/plane measurement geometry, with a cone 20 mm in diameter, an angle of 1 degree and an air gap of 52 microns. The measurement temperature is fixed at 25° C. +/−0.2° C. using a thermostatically-controlled bath but can be adjusted if necessary.

2.3.2 Types of Measurements and Operating Methods

Two complementary types of tests are carried out, on the one hand measurements in static mode and on the other hand measurements in dynamic mode (oscillatory rheology); both are briefly described hereafter.

Static Mode

A flow curve is recorded in static mode $\tau$ shear stress (Pa) as a function of the shear rate $\gamma$ ($s^{-1}$). This curve makes it possible to access information such as the flow behaviour, viscosity, shear stress limit and an optional thixotropy of the samples. The solutions/gels exhibiting peptide nanostructures of nanotube or fibre type in general behave like non-Newtonian fluids. By adapting the theoretical models such as those of Cross (Cross MM. J Colloid Sci 1965 20; 417-37) or Casson (Casson, N. In Rheology of Disperse Systems, C.C. Mill ed, 1959, p. 82, Pergamon Press, New York, N.Y.) to the experimental flow curve it is possible, by extrapolation, to access infinite viscosity ($\eta\infty$) and 0 viscosity, $\eta_0$ (Pa·s) values, which serve as comparison and reference parameters to define the viscosity of these solutions/gels.

Dynamic Mode (Oscillatory Rheology)

For the dynamic measurements, a shear strain ($\gamma_0$) (Pa) of sinusoidal type, of known amplitude and frequency is applied to the sample. The resultant sinusoidal shear stress is measured (amplitude $\tau_0$). The solutions/gels exhibiting peptide nanostructures of nanotube or fibre type are generally viscoelastic systems. In this case, the sine curves recorded for the shear strain and the shear stress having a phase angle difference δ. The values of $\tau_0$, $\gamma_0$ and δ make it possible to access the viscoelastic parameters:

$$\text{The complex modulus } |G^*| = \frac{\tau_0}{\gamma_0}$$

$$\text{The storage modulus } G' = |G^*|\cos\delta$$

$$\text{The loss modulus } G'' = |G^*|\sin\delta$$

The storage modulus (also called elastic modulus) is a measurement of the elastic energy stored (or restored) per unit volume, whilst the loss modulus is a measurement of the energy dissipated per unit volume. These moduli must be calculated in the linear viscoelastic region (i.e. experimental conditions for which these moduli are independent of the amplitude of the shear stress (strain)). These experimental conditions are in general determined by a so-called "stress sweep" experiment which consists of a measurement of the elastic modulus and the loss modulus as a function of the amplitude of the deformation imposed (for a given frequency, typically 1Hz). In general, in the case of small deformations, G' and G" vary very little with the deformation. Then, on passing the yield point, a strong reduction in G' and a maximum of G" is observed. This transition delimits the linear viscoelasticity region. When the linear viscoelasticity region is known, other tests can be carried out such as "frequency sweep" measurements consisting of measuring the dependence of G' and G" as a function of shear frequency at a fixed deformation amplitude, comprised in the linear viscoelasticity region.

The critical deformation is the deformation from which the elastic modulus dependent on the deformation applied at a constant frequency. For higher deformations, the material looses its viscoelastic properties and tends to become more viscous than elastic.

Creep and recovery tests can also be carried out in order to characterize the solutions/gels of the compounds. In this type of test a constant amplitude stress at initial time t=0 is imposed on the sample, which stress is kept constant over time. The zero viscosity, $\eta_0$, is then equal to the inverse of the gradient of the elastic compliance curve (J) as a function of time.

2.3.3 Results

TABLE 2

| Ex | Storage modulus rheology (Pa) | | Critical deformation rheology (Pa) | |
|---|---|---|---|---|
| | 75 mM | 226 mM | 75 mM | 226 mM |
| 3 | Viscosity too low | 150,000 | Viscosity too low | 360 |
| 4 | 184,000 | >2,700,000 | 800 | 18,600 |
| 6 | 643,500 | >2,700,000 | 5000 | 8500 |

2.4 Study of the Release of the Octapeptide Compounds

Release studies can be carried out on the octapeptide compounds according to the invention in the form of gel, solid, or in suspension. Two types of tests can be envisaged: static release tests and/or dynamic tests, both are briefly described hereafter.

The experimental parameters are common to both types of tests. The release medium is a liquid medium which is physico-chemically well-controlled, preferably a PBS (phosphate buffer saline) buffer adjusted to pH 7.4 and maintained at 37° C. The release curve is defined as the concentration of the studied compound in the dissolution medium (expressed in % of free compound) as a function of time (minutes, hours, days). To initiate the tests, a know quantity of sample is placed in the dissolution medium at time 0 (t=0 min/h/d), the sample being optionally conditioned in a device which is suited to its initial physical state (gel, solid, suspension). Measurements of the concentration of the compound in the release medium are carried out by one or more analytical methods which are well known in the state of the art such as UV-visible spectrophotometry or the HPLC (High Performance Liquid Chromatography). The parameters of the analytical methods are adjusted as a function of the physico-chemical characteristics of the compounds. The tests can be carried out with various starting concentrations such as 75 mM and 226 mM in the examples presented hereafter.

2.4.1 Static Tests

The studies of release in static mode are carried out without subjecting the samples to controlled stirring or to a release medium flow. The samplings of release medium and/or the determinations of concentration are generally not automated and require manual operations. For example, certain static release studies can be carried out on samples corresponding to approximately 2 to 5 mg of pure compound in 20 mL of PBS (typically in 50 mL beakers) maintained in an oven at 37° C. The concentration measurements are carried out on representative samplings of the release medium carried out at chosen times.

2.4.2 Dynamic Tests

For the dynamic release studies, controlled stirring or a release medium flow is applied to the samples. In this mode, the samplings and/or concentration determinations are generally automated and the studies can be carried out in systems / instruments which are standardized and well known in the state of the art (cf. European Pharmacopeia systems). For example, certain studies in dynamic mode can be carried out on samples corresponding to the order of 10 mg of pure compound placed in 100 mL of PBS introduced beforehand into standardized beakers and maintained at 37° C. The stirring and samplings / measurements are controlled by a dissolution testing instrument of device type 1 or 2 described by the European Pharmacopeia.

2.4.3 Results

TABLE 3

| | Static release after 48 h | Dynamic release after 44 h | |
|---|---|---|---|
| Ex | 75 mM | 75 mM | 226 mM |
| 3 | / | 100% | 93% |
| 4 | 85% | 94% | 75% |
| 6 | 25% | 37% | 17% |

2.5 Analysis of the Experimental Results

Therefore, the biological and/or physico-chemical properties of the compounds of the invention make it possible to envisage various applications such as peptides having a therapeutic activity with an immediate or sustained effect, or peptides without an intrinsic therapeutic effect but serving as a formulation support for example for a sustained release of active ingredient.

The invention claimed is:

1. A compound of formula (I) or a pharmaceutically acceptable salt thereof:

$$\text{H-2-Nal}^1\text{-cyclo}(\text{Cys}^2\text{-Tyr}^3\text{-AA}^4\text{-Lys}^5\text{-Val}^6\text{-Cys}^7)\text{-Thr}^8\text{-NH}_2 \quad \text{(I)(SEQ ID NO: 1)}$$

wherein $AA^4$ is an amino acid radical bound to the amino acids $Tyr^3$ and $Lys^5$ according to the formula:

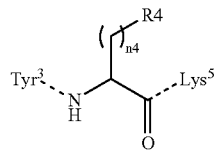

wherein n4 is 0 or 1 and

R4 is a hydrogen atom or an alkyl radical; and any of the amino acids can be in the D configuration.

2. The compound of claim 1, wherein n4 is 0 and R4 is an alkyl radical.

3. The compound of claim 1, wherein the alkyl radical is a methyl, ethyl, propyl, isopropyl, butyl, isobutyl, or tert-butyl.

4. The compound of claim 1, wherein $AA^4$ is the amino acid radical Ala.

5. The compound of claim 1, wherein the compound is H-D-2-Nal$^1$-cyclo (Cys$^2$-Tyr$^3$-D-Ala$^4$-Lys$^5$-Val$^6$-Cys$^7$)-Thr$^8$-NH$_2$; or H-D-2-Nal$^1$-cyclo (Cys$^2$-Tyr$^3$-D-Val$^4$-Lys$^5$-Val$^6$-Cys$^7$)-Thr$^8$-NH$_2$; or a pharmaceutically acceptable salt thereof.

6. The compound of claim 5, wherein the compound is H-D-2-Nal$_1$-cyclo(Cys$^2$-Tyr$^3$-D-Val$^4$-Lys$^5$-Val$^6$-Cys$^7$)-Thr$^8$-NH$^2$or a pharmaceutically acceptable salt thereof.

7. The compound of claim 5, wherein the compound is: H-D-2-Nal$^1$-cyclo(Cys$^2$-Tyr$^3$-D-Ala$^4$-Lys$^5$-Val$^6$-Cys$^7$)-Thr$^8$-NH$_2$ or a pharmaceutically acceptable salt thereof.

* * * * *